(12) United States Patent
Wilson

(10) Patent No.: US 8,763,971 B1
(45) Date of Patent: Jul. 1, 2014

(54) RESPIRATORY VENTILATOR TRANSPORT SYSTEM

(71) Applicant: Dan Duncan Wilson, West End, NC (US)

(72) Inventor: Dan Duncan Wilson, West End, NC (US)

( * ) Notice: Subject to any disclaimer, the term of this patent is extended or adjusted under 35 U.S.C. 154(b) by 0 days.

(21) Appl. No.: 13/920,916

(22) Filed: Jun. 18, 2013

Related U.S. Application Data

(62) Division of application No. 12/008,953, filed on Jan. 15, 2008, now abandoned.

(60) Provisional application No. 60/880,216, filed on Jan. 16, 2007, provisional application No. 60/901,298, filed on Feb. 15, 2007.

(51) Int. Cl.
*B42F 13/00* (2006.01)

(52) U.S. Cl.
USPC ............ 248/340; 248/317; 248/339; 248/690; 248/341; 211/113; 220/23.89; 220/23.87; 220/668; 206/514

(58) Field of Classification Search
CPC .......................... A47F 5/0006; A61G 7/0503
USPC ......... 248/317, 339, 340, 690, 674, 146, 153, 248/311.2, 27.8, 341; 220/23.89, 23.87, 220/23.91, 668; 211/85.6, 113, 119.004; 206/514
See application file for complete search history.

(56) References Cited

U.S. PATENT DOCUMENTS

| | | | | |
|---|---|---|---|---|
| 890,354 A * | 6/1908 | Giard | ........................... | 220/17.3 |
| 1,181,377 A | 5/1916 | Dowell | | |
| 2,763,413 A * | 9/1956 | Felton | ........................... | 224/411 |
| 2,957,667 A * | 10/1960 | Kughler | ......................... | 248/339 |
| 3,391,891 A * | 7/1968 | Garden | ........................ | 248/311.2 |
| 3,586,276 A | 6/1971 | O'Mahoney | | |
| 3,920,211 A | 11/1975 | Knight | | |
| 3,995,803 A * | 12/1976 | Uitz | ............................... | 224/432 |
| 4,101,109 A | 7/1978 | Edwards | | |
| 4,267,997 A * | 5/1981 | Meier | ........................... | 220/491 |
| 4,747,843 A * | 5/1988 | Felix et al. | ..................... | 604/318 |
| 4,756,501 A * | 7/1988 | Quercia et al. | ................ | 248/340 |
| 5,131,620 A | 7/1992 | Boundy | | |
| 5,282,599 A * | 2/1994 | Arpaia et al. | ............... | 248/311.2 |
| 5,393,025 A | 2/1995 | Franklin | | |
| 5,393,113 A * | 2/1995 | Walsh | ........................... | 294/170 |
| 6,065,727 A * | 5/2000 | Fitzgerald et al. | ............ | 248/302 |
| 6,098,944 A | 8/2000 | Pangborn et al. | | |
| 6,368,311 B1 * | 4/2002 | Valerio et al. | .................. | 604/322 |
| 6,488,246 B2 | 12/2002 | Song | | |
| 6,986,491 B2 | 1/2006 | Anderson | | |
| 7,232,105 B2 * | 6/2007 | Want et al. | ..................... | 248/691 |
| 2004/0031897 A1 | 2/2004 | Holland | | |
| 2009/0184077 A1 | 7/2009 | Curet et al. | | |

* cited by examiner

*Primary Examiner* — Anita M King
*Assistant Examiner* — Michael McDuffie
(74) *Attorney, Agent, or Firm* — Smith Moore Leatherwood LLP; Thomas W. Epting

(57) ABSTRACT

A system for carrying a respiratory ventilator and respiratory ventilator power supply on a support. The support may be fixed or inclinable, and the device includes at lease one body portion having a first receiver that receives the respiratory ventilator and a second receiver that receives the respiratory ventilator power supply. A coupling is connected to the body portion that attaches the body portion to the support. The coupling is configured to cause the body portion to incline in response to, and generally to the same extent as, inclination of the support in order to present a relatively low profile to the surroundings.

8 Claims, 32 Drawing Sheets

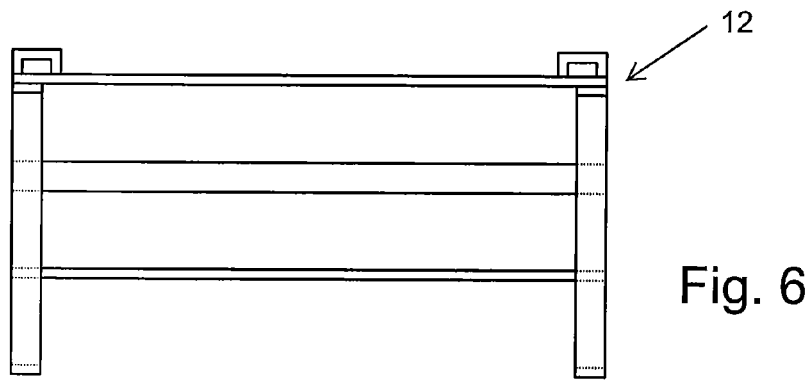
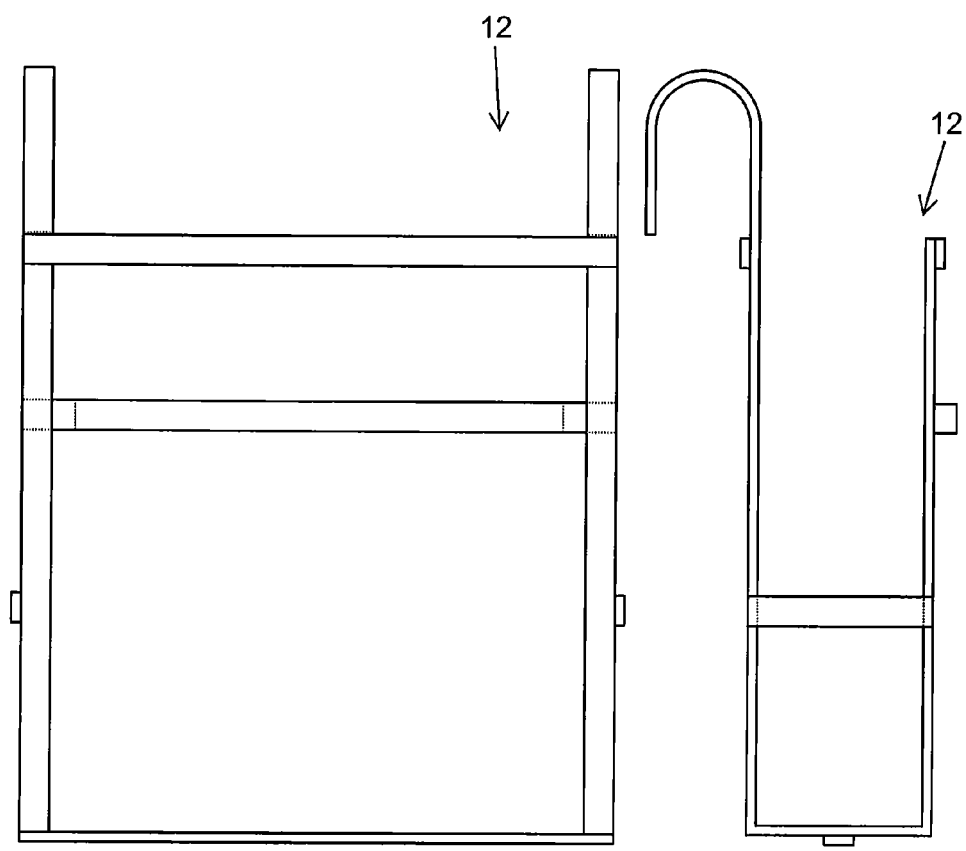
Fig. 6
Fig. 7          Fig. 8

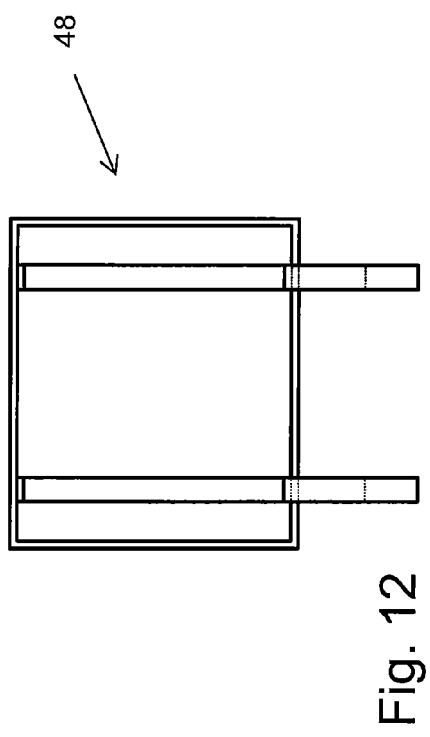
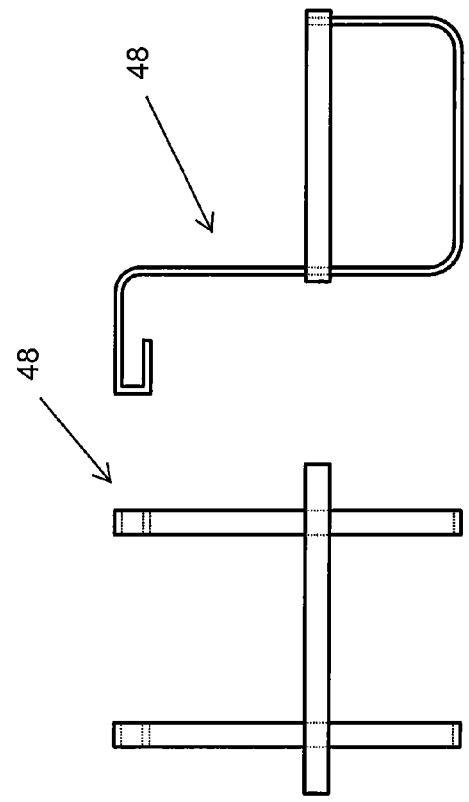
Fig. 12
Fig. 13
Fig. 14

RESPIRATORY VENTILATOR TRANSPORT SYSTEM

This application is a divisional and claims benefit of non-provisional application Ser. No. 12/008,953, filed Jan. 15, 2008, which claims benefit of U.S. Provisional application Ser. No. 60/880,216, filed Jan. 16, 2007, and U.S. Provisional application Ser. No. 60/901,298, filed Feb. 15, 2007, and the entirety of each of the foregoing applications is incorporated herein by reference.

BACKGROUND OF THE INVENTION

This invention relates generally to a system for transporting a respiratory ventilator and power supply to facilitate mobility of a patient.

Respiratory ventilators, also referred to herein as simply, "ventilators," may be necessary for use by a patient on a temporary and/or long term basis. Ventilators move air into and out of the patient's lungs to provide respiration for a patient who is physically unable to breathe adequately on their own. In many cases, a patient on a ventilator remains in the intensive or otherwise heighted-care portion of a medical facility.

Such ventilators may, because of their construction and mode of operation, require the patient to remain in or near a health care facility under the care of health care providers. In certain situations, with proper training of attending personnel and in an appropriate environment, a patient may be permitted to live at home, with such ventilator system being monitored there.

Ventilators typically require electrical power, such as alternating current (AC) or direct current (DC) power, and include the use of flexible tubes for supplying air to the patient and for return air from the patient.

There exists a need, however, for a way in which a patient requiring ventilator support can attain mobility while simultaneously being supported by the ventilator, and thus potentially greatly enhance the quality of his or her life.

SUMMARY OF THE INVENTION

Generally, one preferred embodiment of the present invention includes a device for carrying a respiratory ventilator on a support, the support being static or inclinable. The device includes, but is not limited to, a body portion defining a receiver that receives the respiratory ventilator and a coupling connected to the body portion that attaches the body portion to the support. The coupling is configured to cause the body portion to incline in response to, and generally to substantially the same extent as, the inclination of the support.

In one preferred embodiment, the coupling is of a generally hook shape, and the body member is of an open frame, or framework, configuration. For example, the body member may include four upright rails, a bottom rail, two side rails, a front rail, and a rear rail, with the upright, bottom, side, front, and rear rails being configured to form an open frame configuration defining the receiver. Additionally, a strap may be connected to the body member that holds the respiratory ventilator in the receiver.

In a preferred embodiment, the body member defines a front, a back, and a bottom and a centerline extending between the front and the back which is generally perpendicular to the bottom. In this embodiment, the back defines an upper portion and a lower portion, and the coupling is spaced away from the centerline and attached to the upper portion of the back.

In a further preferred embodiment, the coupling is a hook that engages the support, and a pivotal connector permits the hook to pivot with respect to the body member between a locked position and an unlocked position. A spring biases the hook towards the locked position.

The present invention also includes a device for carrying a respiratory ventilator system component, such as a battery, ventilator sub-system, etc., on a support and includes a body portion defining a receiver that receives the respiratory ventilator power supply and at least one coupling connected to the body portion that attaches the body portion to the support. The coupling is configured to cause the body portion to incline in response to, and generally to the same extent as, inclination of the support.

Additionally, the present invention includes a method of transporting a respiratory ventilator and a power supply therefor.

BRIEF DESCRIPTION OF THE DRAWINGS

The foregoing, as well as other objects of the present invention, will be further apparent from the following detailed description of the preferred embodiment of the invention, when taken together with the accompanying specification and the drawings, in which:

FIG. 6 is a plan view of the ventilator carrier shown in FIG. 1;

FIG. 7 is a front elevational view of the ventilator carrier shown in FIG. 1;

FIG. 8 is a left side elevational view of the ventilator carrier shown in FIG. 1;

FIG. 12 is a plan view of the ventilator power supply carrier shown in FIG. 10;

FIG. 13 is a front elevational view of the ventilator power supply carrier shown in FIG. 10;

FIG. 14 is a left side elevational view of the ventilator power supply carrier shown in FIG. 10;

DESCRIPTION OF THE PREFERRED EMBODIMENT

Figure 1:
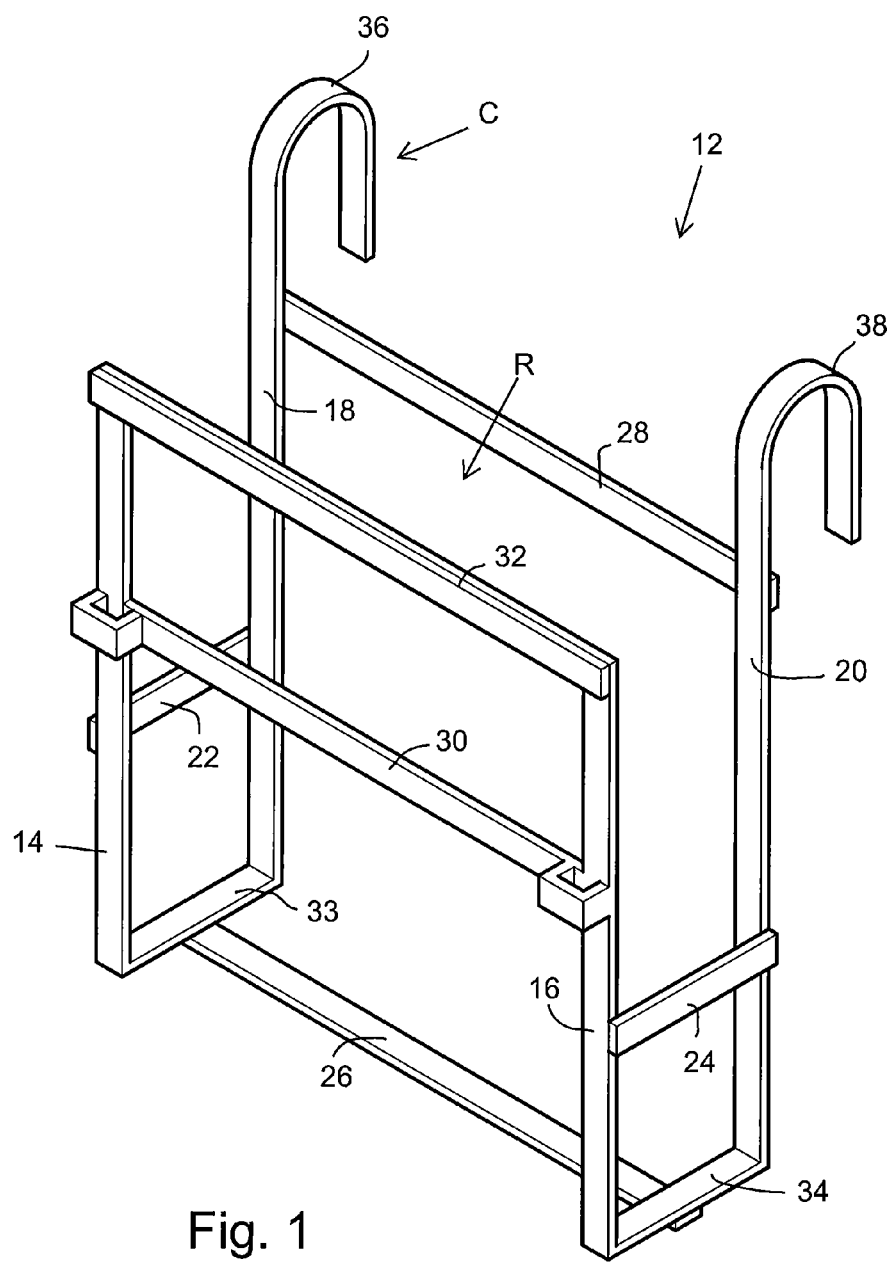
FIG. 1 is a perspective view of one preferred embodiment of a ventilator carrier constructed in accordance with the present invention.

The foregoing, as well as other objects of the present invention, will be further apparent from the following detailed description of the preferred embodiment of the invention, when taken together with the accompanying drawings and the description which follows set forth this invention in its preferred embodiment. However, it is contemplated that persons generally familiar with respiratory ventilator systems will be able to apply the novel characteristics of the structures illustrated and described herein in other contexts by modification of certain details. Accordingly, the drawings and description are not to be taken as restrictive on the scope of this invention, but are to be understood as broad and general teachings.

Referring now to the drawings in detail, wherein like reference characters represent like elements or features throughout the various views, the respiratory ventilator transport system of the present invention is discussed.

Turning now to FIGS. 1 through 9C, one preferred embodiment of a respiratory ventilator carrier, generally 12, is shown. Carrier 12 includes a generally open framework structure having front uprights 14, 16, rear uprights 18, 20, side members 22, 24, a bottom member 26, a back member 28, front members 30, 32 and bottom side members 33 and 34. Carrier 12 could be constructed of metal bar stock, plastic, wood, or any other suitable material. It could also be welded, molded, cast, and/or a combination thereof.

Figure 9C:
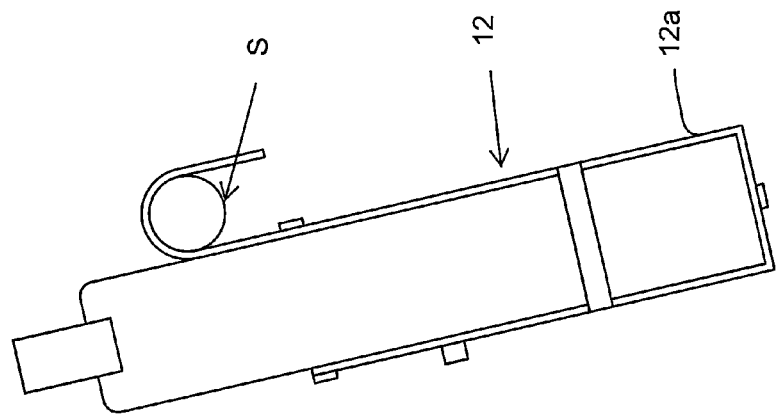
FIGS. 9A-9C are right side elevational views of the ventilator carrier shown in FIG. 1, being installed on a support and pivoting in response to movement of the support.
Figure 9B:
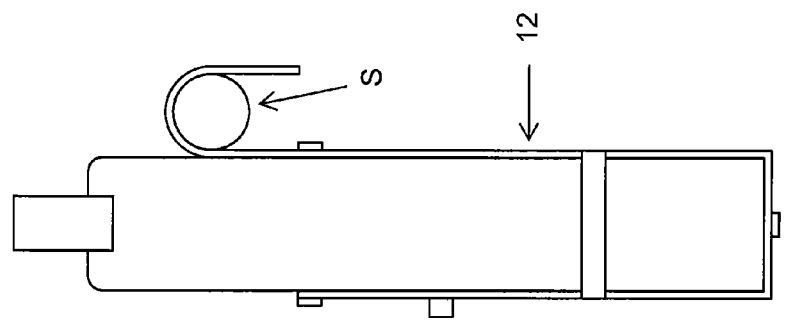
Figure 9A:
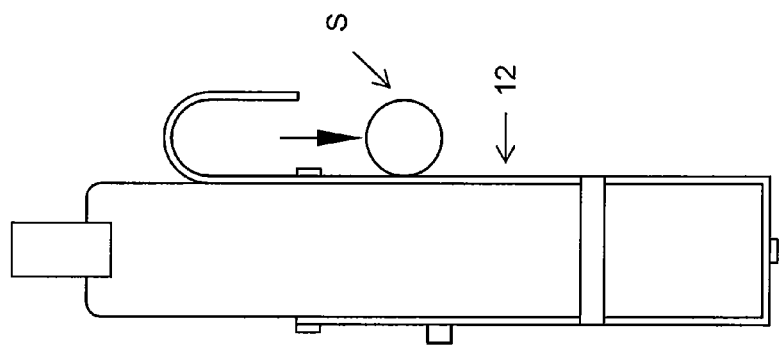

Rear uprights 18, 20 each terminate in a semi-circular hook-shaped portion, generally 36 and 38, such portions 36 and 38 forming a coupling, or, connector, generally C, which is used to attach carrier 12 to a support member, generally S, such as shown in FIGS. 9A, 9B, and 9C.

Figure 2:
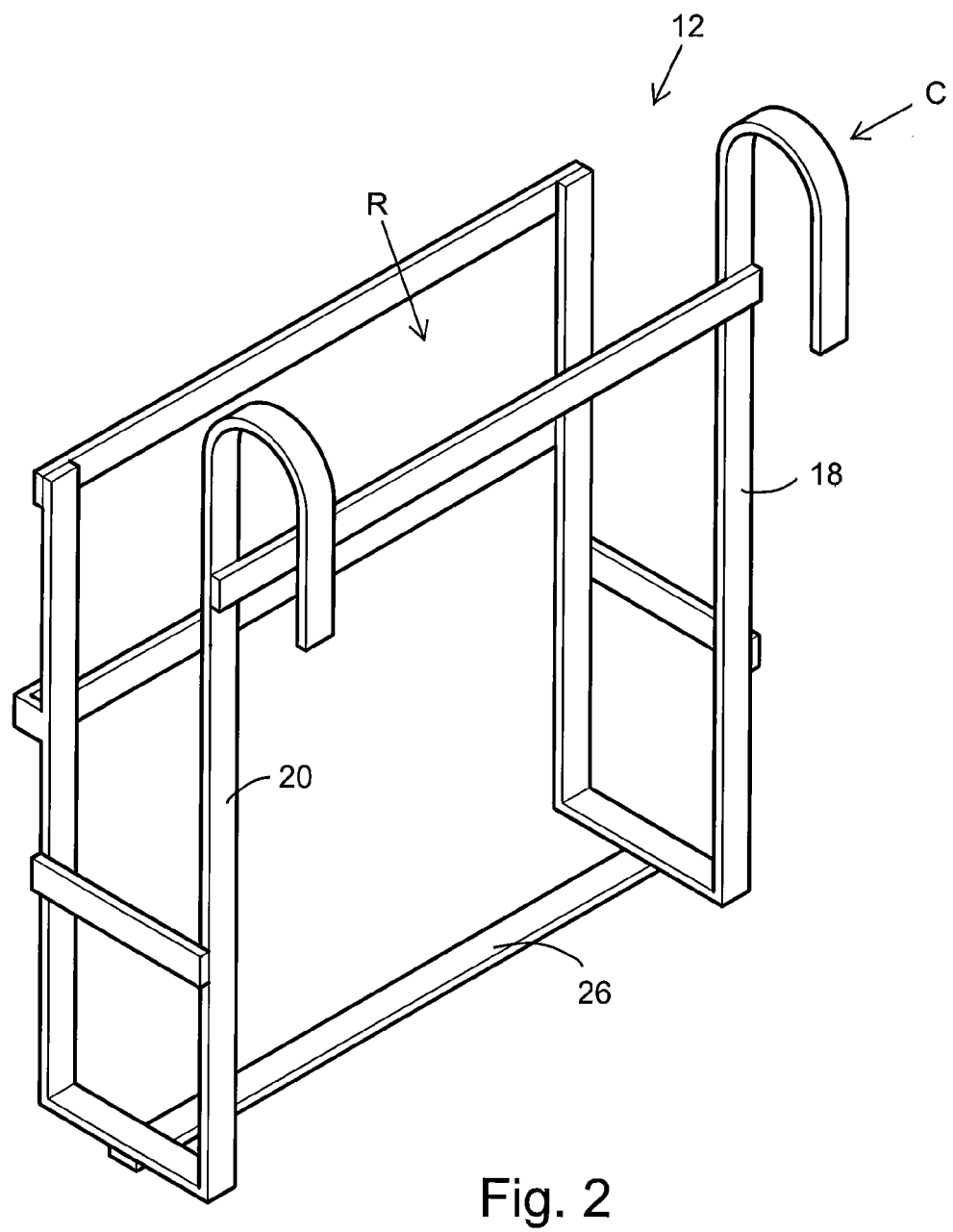
FIG. 2 is a perspective view of the ventilator shown in FIG. 1.
Figure 3:
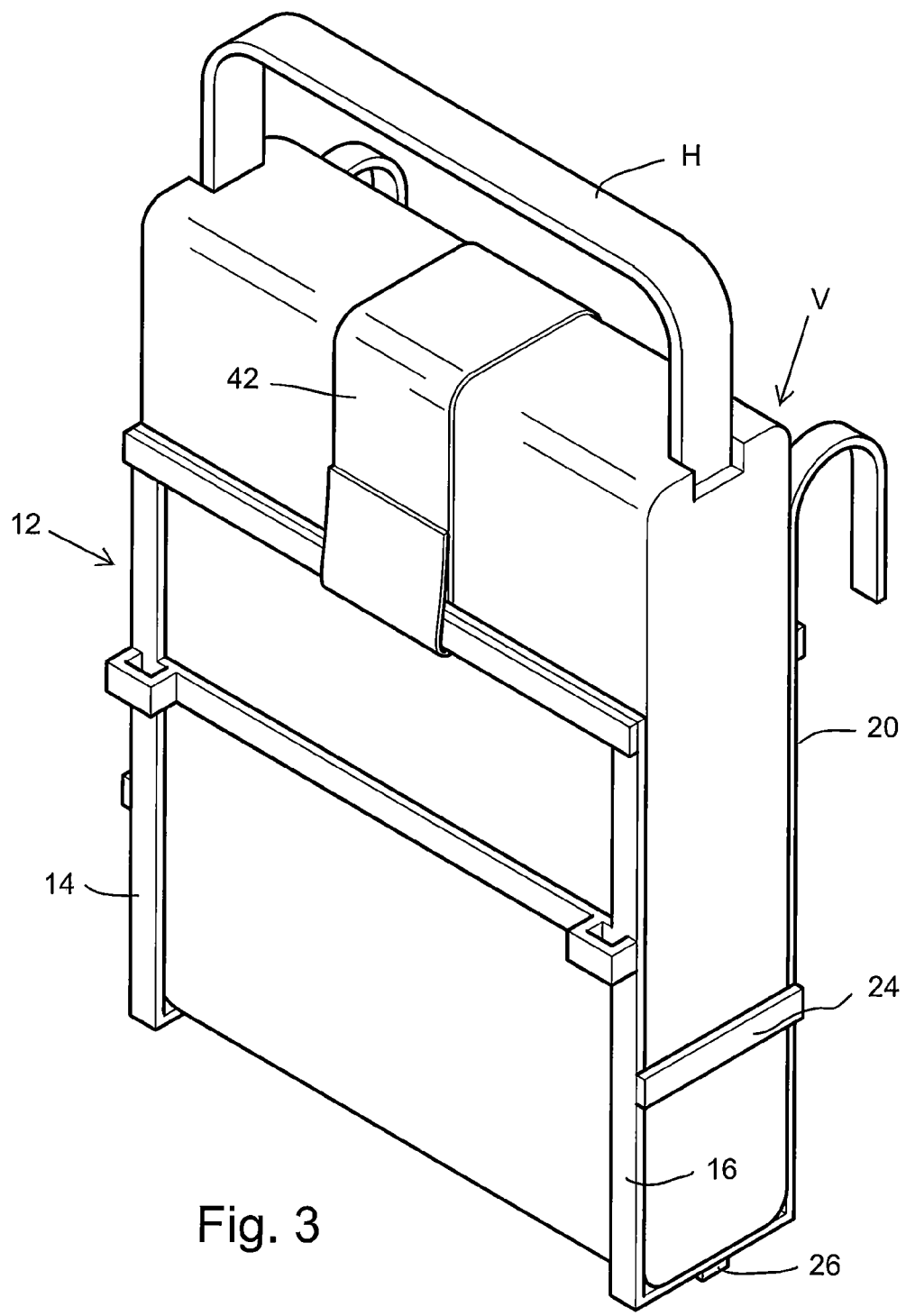
FIG. 3 is a front perspective view of the ventilator carrier shown in FIG. 1, having a ventilator positioned therein.
Figure 4:
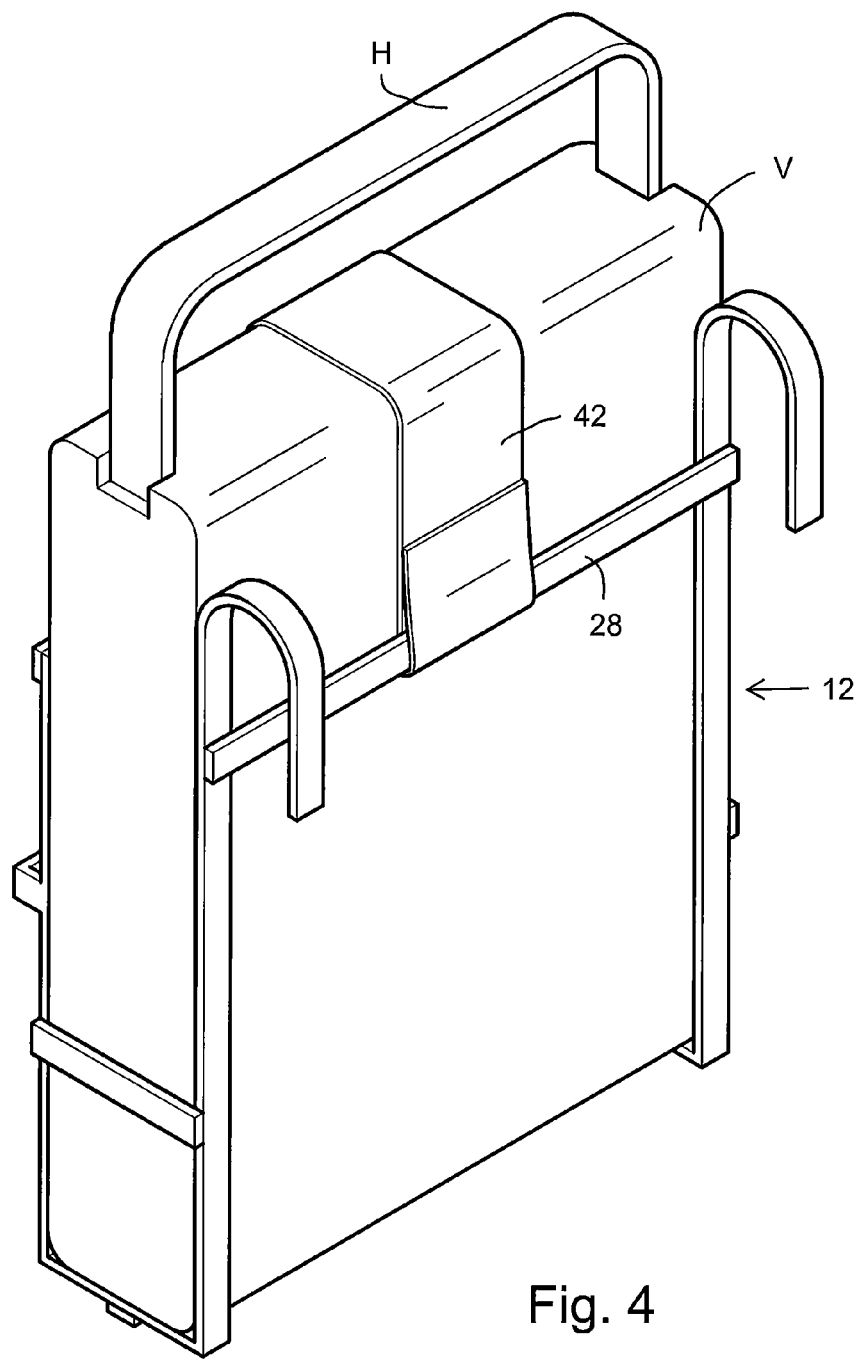
FIG. 4 is a rear perspective view of the ventilator carrier shown in FIG. 1, having a ventilator positioned therein.
Figure 5:
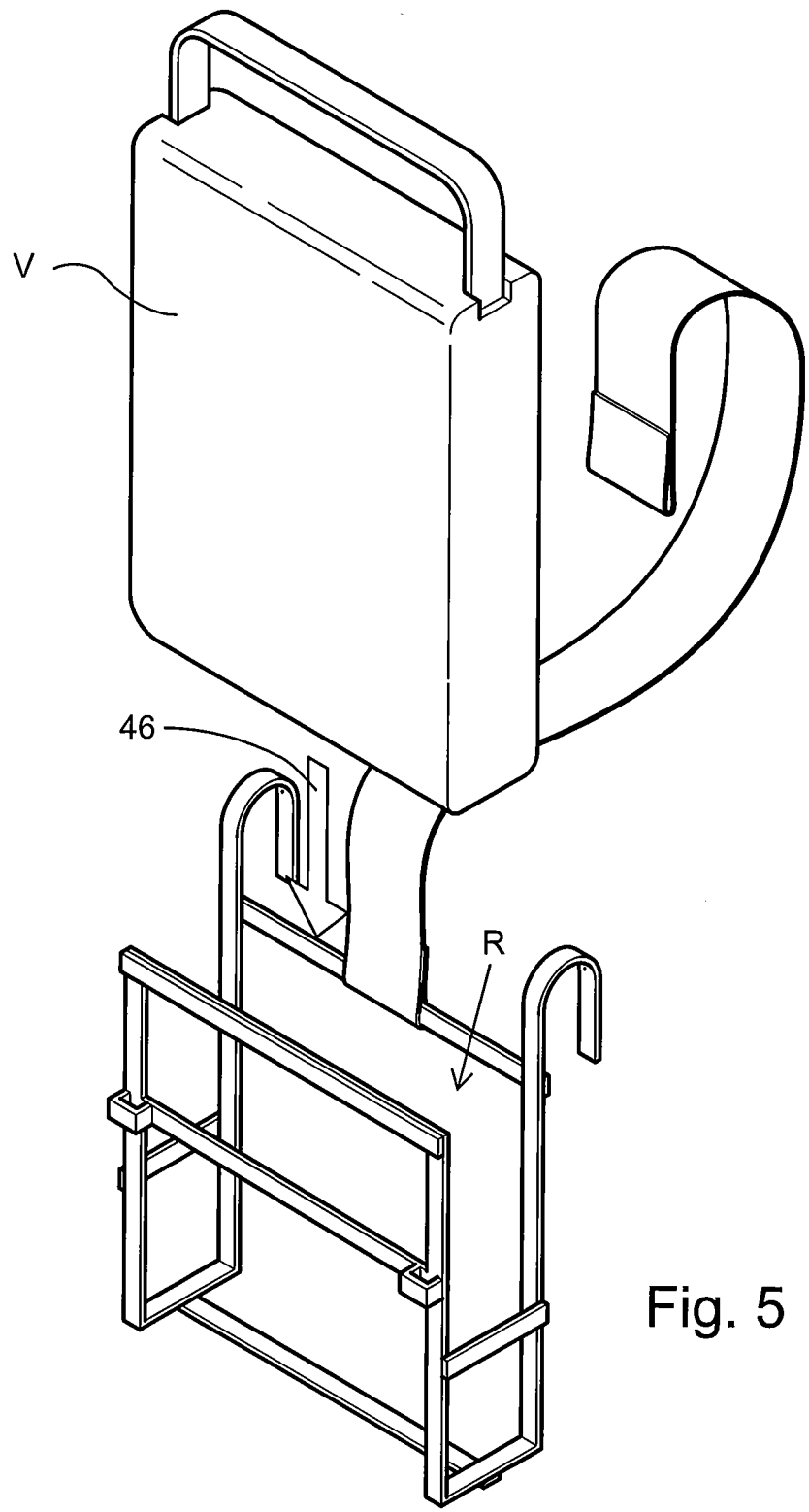
FIG. 5 is a perspective view of the ventilator carrier shown in FIG. 1, with a ventilator in the process of being positioned therein.

FIGS. 1 and 2 show carrier 12 from the front, and from the rear, respectively, and FIG. 3 illustrates carrier 12 having a respirator ventilator, generally V, received within a receiver portion, generally R, formed by front uprights 14, 16, rear uprights 18, 20, side members 22, 24, bottom member 26, front members 30, 32, and back member 28. A retaining strap, generally 42, is connected to front member 32 and passes over the top of respiratory ventilator V, and terminates at a connection to back member 28 (FIG. 4) of carrier 12. Retaining strap 42 serves to secure ventilator V to carrier 12 when desired, and is readily releasable, in the event it is desired to remove ventilator V from receiver R. In such an event, ventilator V would typically be withdrawn from receiver R using handle H of ventilator V. FIG. 5 illustrates strap 42 having one end removed from carrier 12 for allowing ventilator V to be inserted into receiver R in the direction by arrow 46.

FIGS. 6, 7 and 8 illustrate carrier 12 in a plan view, front elevational view, and left side elevational view, respectively.

FIG. 9A illustrates carrier 12 being connected to support member S, which could be a bar or tube such as found on a movable conveyance, such as a wheelchair, hospital bed, cart, gurney, vehicle, or on a stretcher, lift, handrail, structural member, etc. for supporting carrier 12 and the ventilator V therein. FIG. 9A illustrates how carrier 9A is positioned on support member S with hook-shaped coupling C being placed onto support member S. FIG. 9B illustrates carrier 12 and ventilator V being supported on support member S via coupling C.

Figures 40A, 40B:
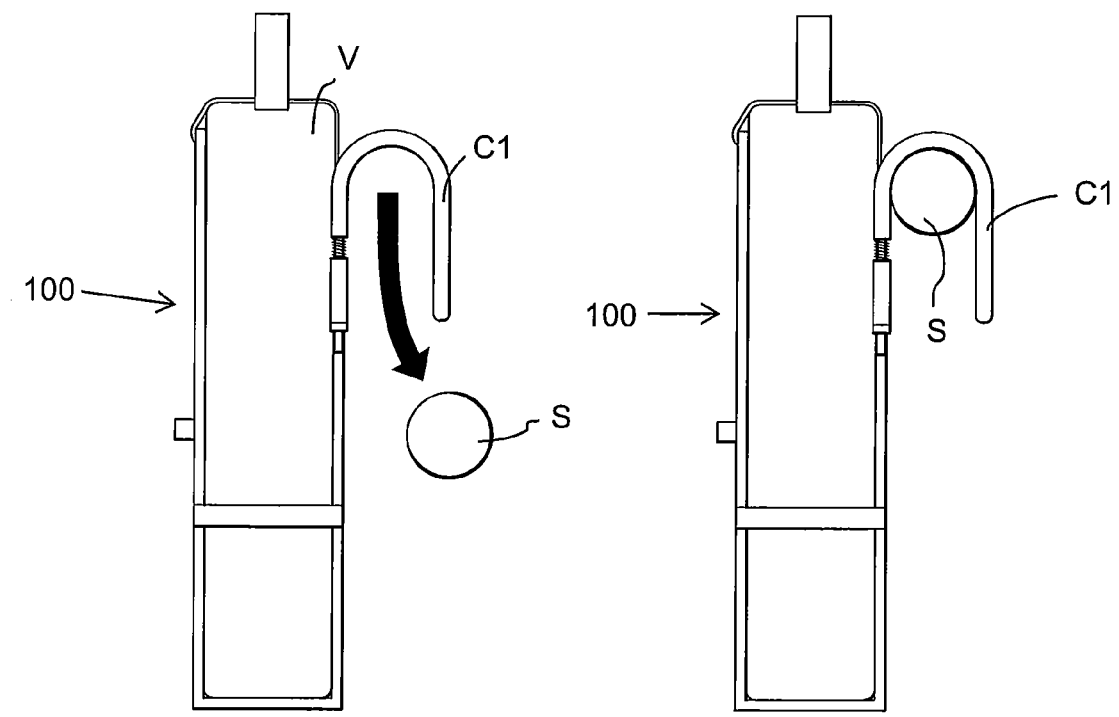
FIGS. 40A-40C are right side elevational views of the ventilator carrier shown in FIG. 15 with a ventilator therein and being installed on a support, and pivoting in response to movement of the support.
Figure 40C:
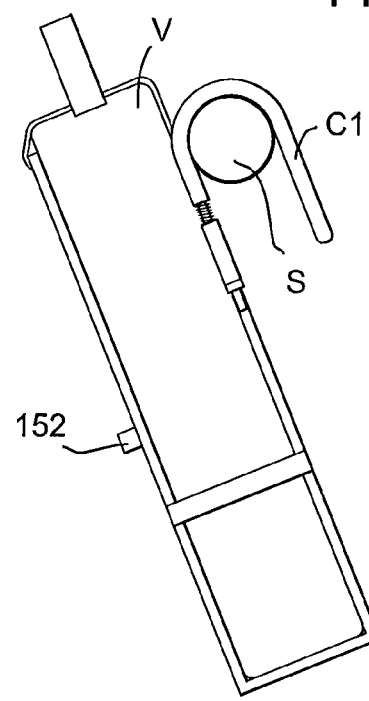

FIG. 9C illustrates the orientation of carrier 12 and ventilator V in the event support member S is moved in a counterclockwise direction with respect to the position shown in FIG. 9B. As support member S is moved in such counterclockwise ventilation, carrier C and ventilator V therein likewise pivot in a similar manner and generally to the same extent to minimize relative movement or swinging, of carrier C with respect to support member S. For example, in the event carrier C is connected to a support S the back of a reclinable wheelchair (not shown), and such wheelchair is reclined rearwardly, carrier 12 would experience little pivoting relative to support S on the back of the wheelchair, i.e., the bottom portion 12a of carrier 12 would tend to pivot in a counterclockwise direction generally to the same extent as support member S moves in a counterclockwise direction, within a predetermined range of motion of support member S. FIGS. 40A, 40B, and 40C illustrate the same motion of an alternate embodiment ventilator carrier 100, discussed below, as support member S moves in a counterclockwise direction.

Figure 10:
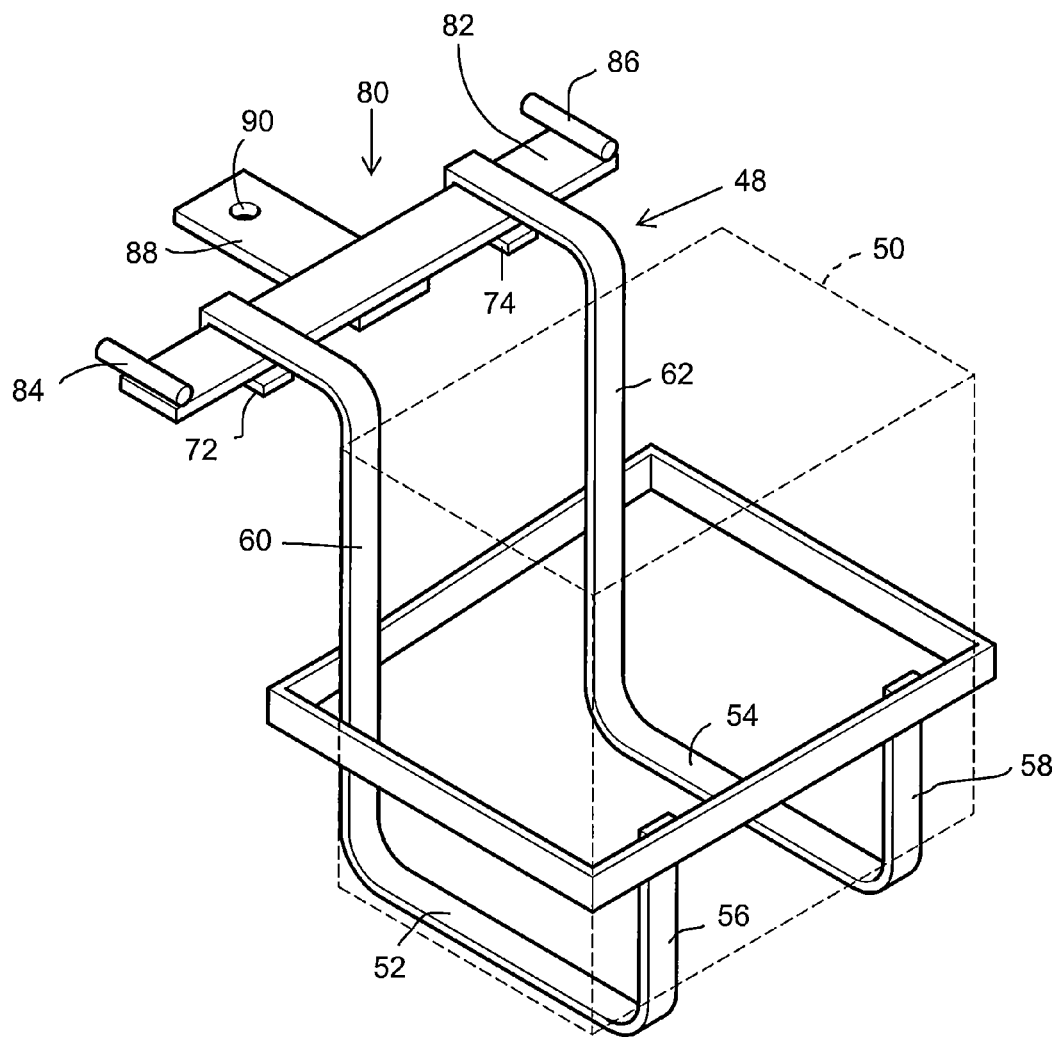
FIG. 10 is a perspective view of one preferred embodiment of a ventilator power supply carrier constructed in accordance with the present invention.

FIGS. 10 through 14 illustrate a power supply carrier, generally 48, as shown in FIG. 10. A power supply 50 is typically a battery, but could be another type of power supply, such as a fuel cell, generator, solar reflector, etc. For example, a conventional battery may provide eight to ten hours of power for a particular ventilator V.

Carrier 48 includes bottom members 52, 54, front upright portions 56, 58, rear upright portions 60, 62, front and rear members 64, 66, side members 68, 70, and hook-shaped connector, or coupling, portions, generally 72 and 74. A bracket, generally 80, may be provided to which coupling portions 72, 74, are attached, although it is to be understood that couplings 72, 74 could be connected to structures other than bracket 80 disclosed herein.

Bracket 80 includes a transverse member 82 having stops 84, 86 provided at the ends thereof. Transverse member 82 is connected to a connector plate, generally 88 which may include a hole 90 for attaching bracket 80 to a structure through use of a bolt, screw, pin, clip, or other suitable fastener (none shown).

Figure 11:
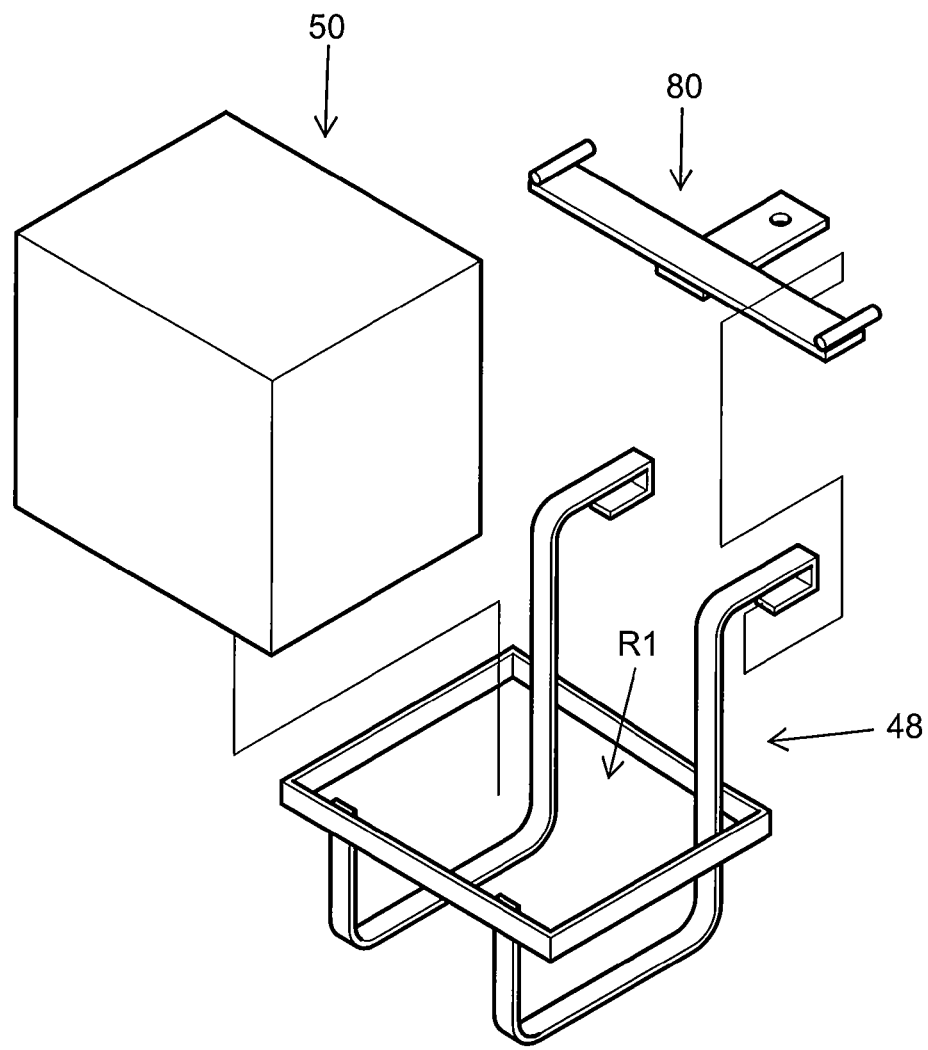
FIG. 11 is an exploded view of the ventilator power supply carrier shown in FIG. 10, a power supply, and a mounting bracket constructed in accordance with the present invention.
Figure 15:
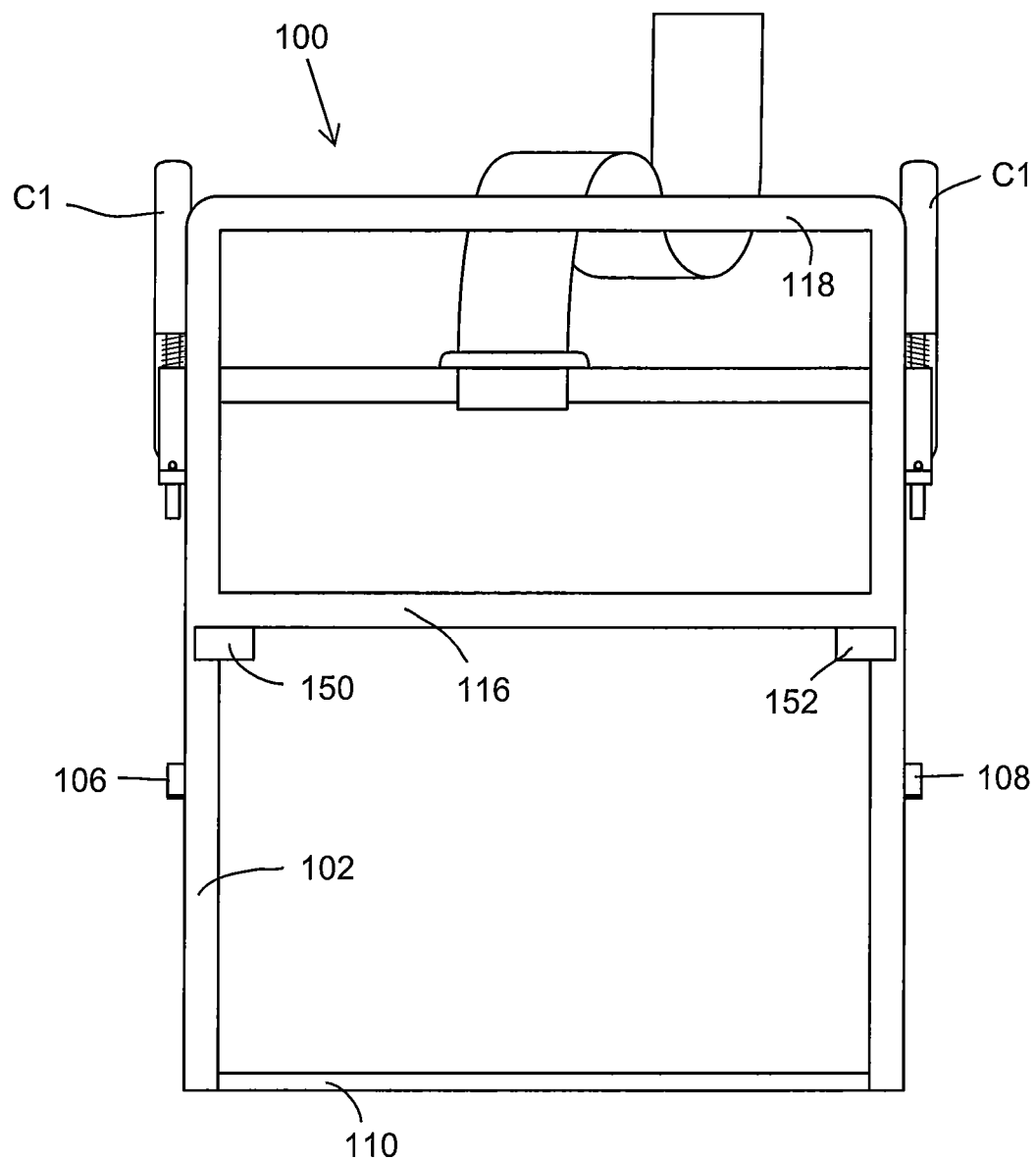
FIG. 15 is a front elevational view of an alternate embodiment of a ventilator power supply carrier constructed in accordance with the present invention.
Figures 16, 17:
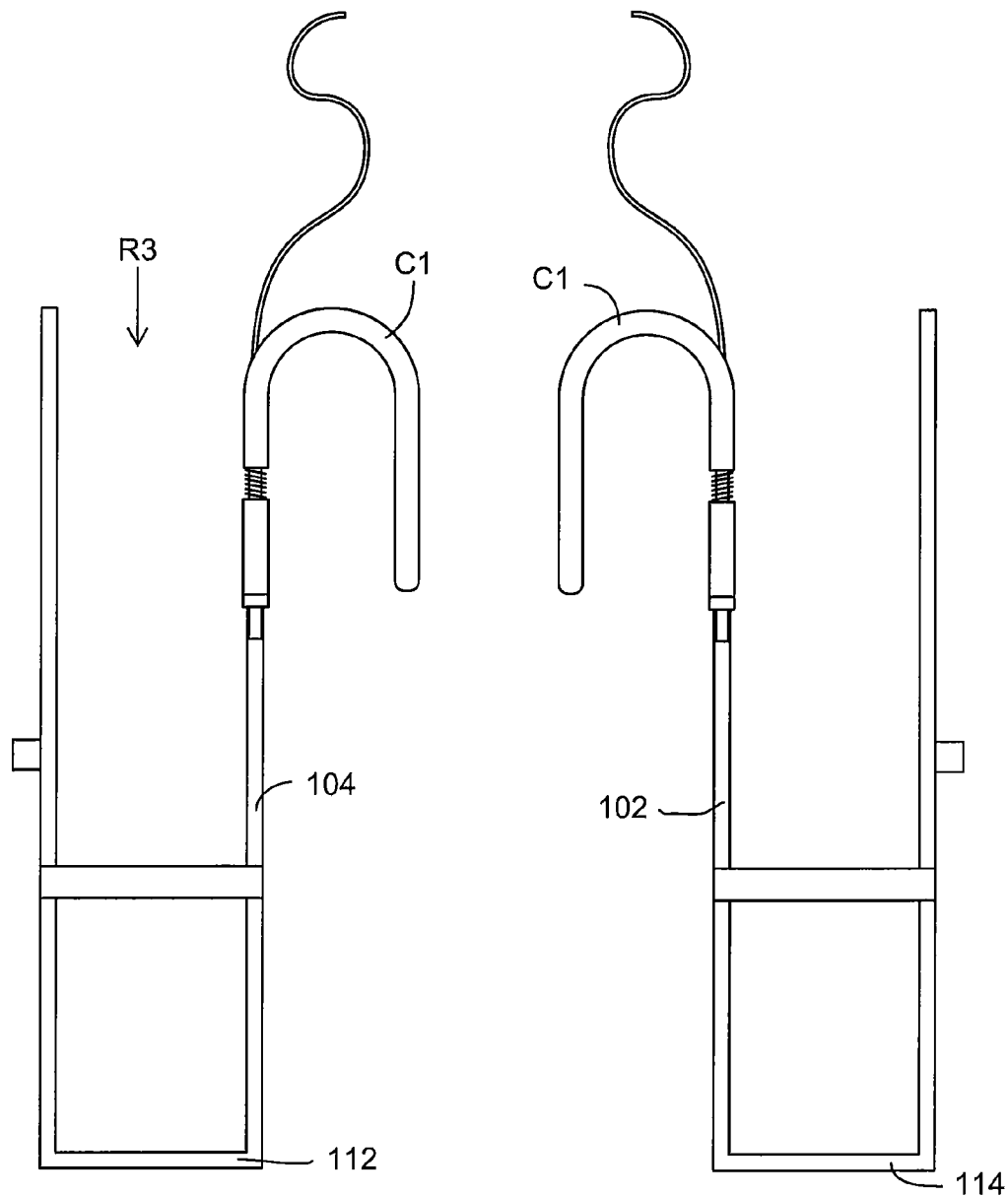
FIG. 16 is a right side elevational view of the ventilator carrier shown in FIG. 15.
FIG. 17 is a left side elevational view of the ventilator carrier shown in FIG. 15.
Figure 18:
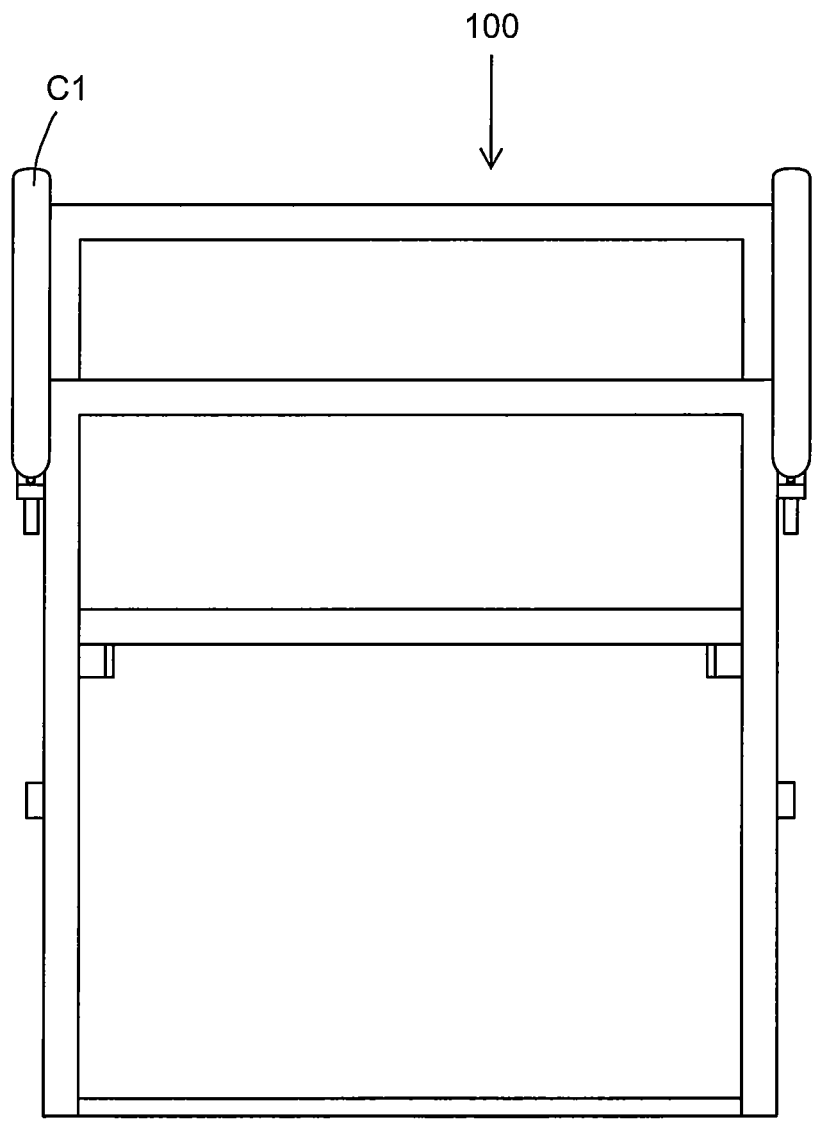
FIG. 18 is a rear elevational view of the ventilator carrier shown in FIG. 15.
Figure 19:
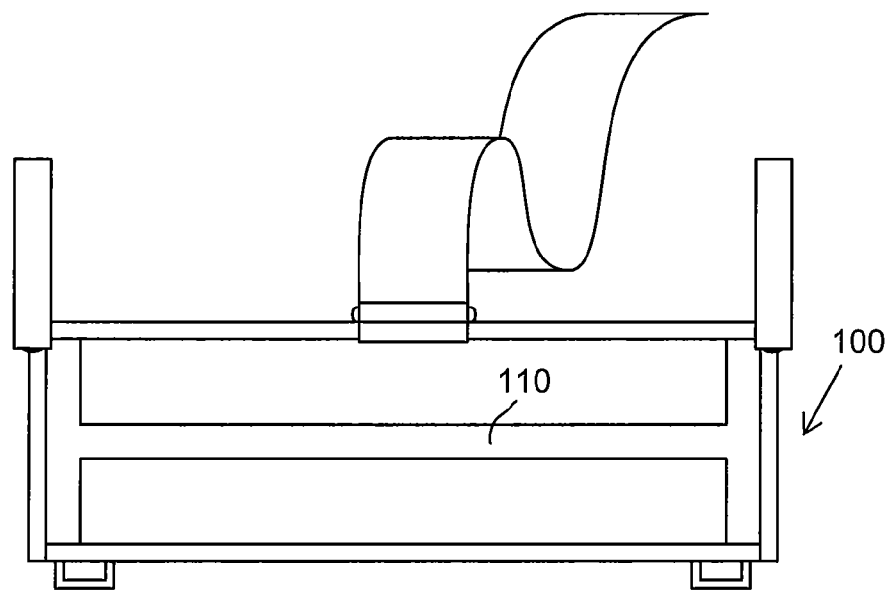
FIG. 19 is a top plan view of the ventilator carrier shown in FIG. 15.
Figure 20:
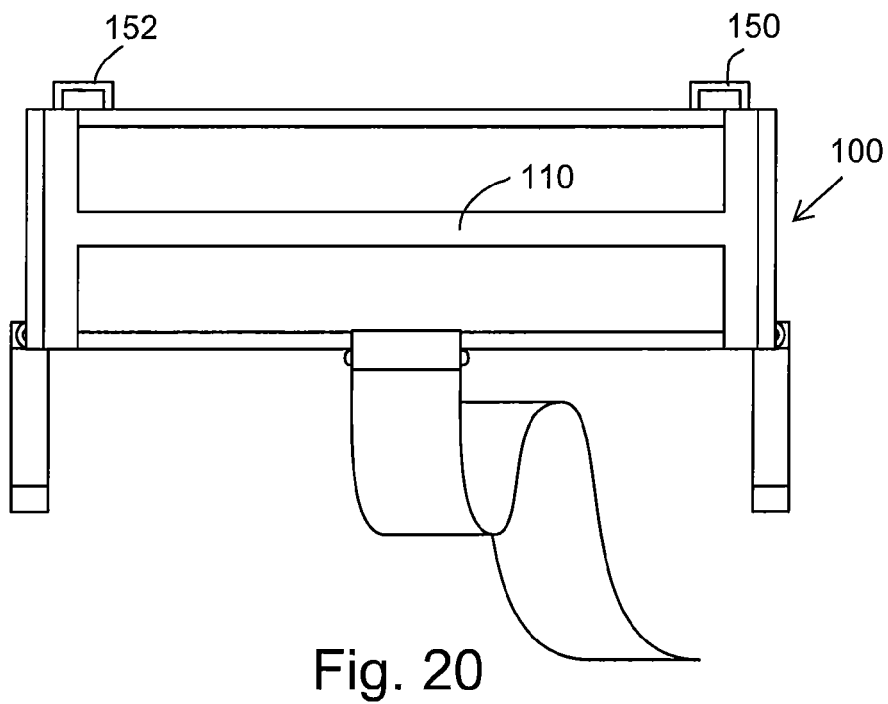
FIG. 20 is a bottom plan view of the ventilator carrier shown in FIG. 15.
Figure 21:
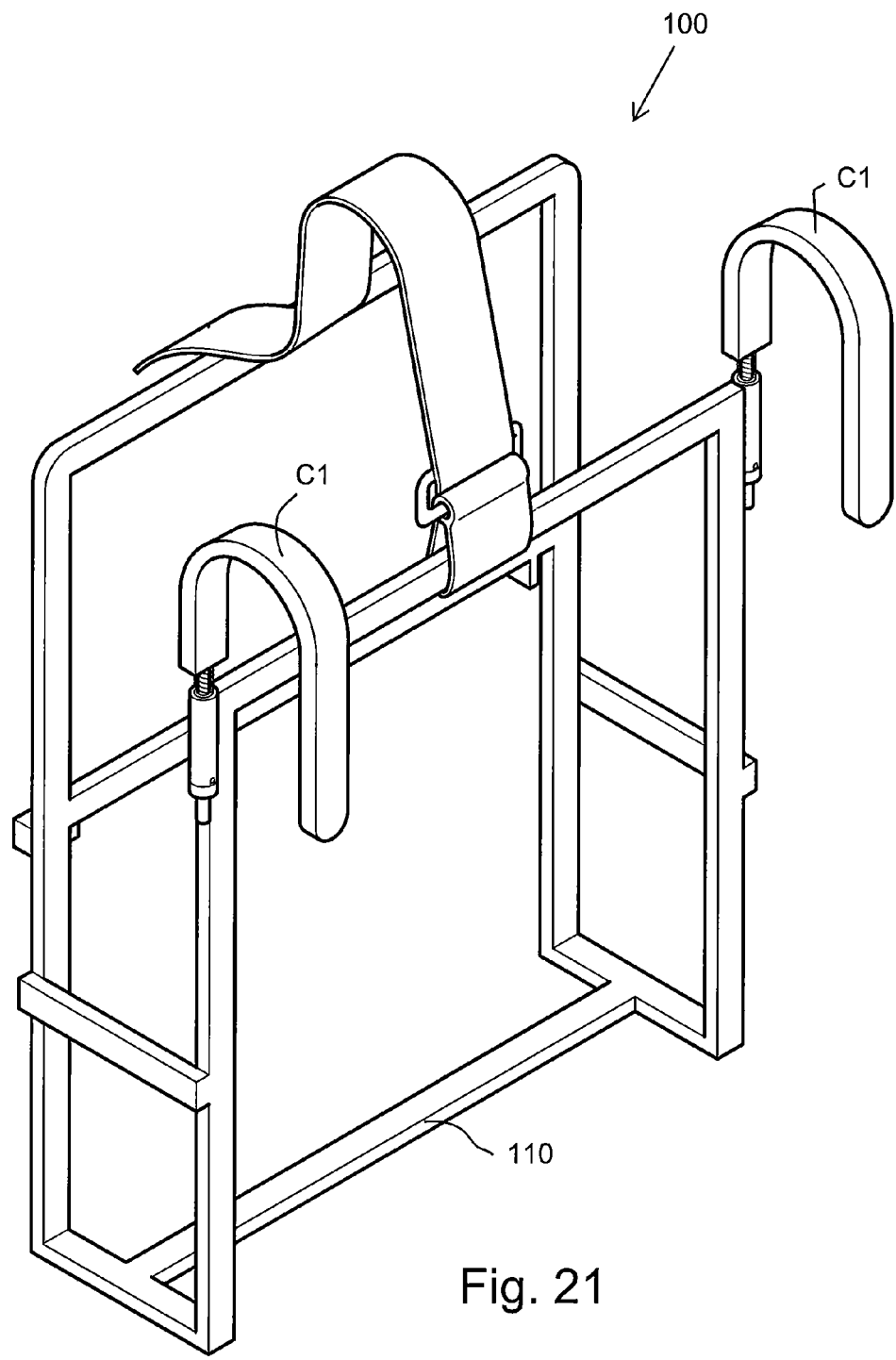
FIG. 21 is a rear perspective view of the ventilator carrier shown in FIG. 15.
Figure 22:
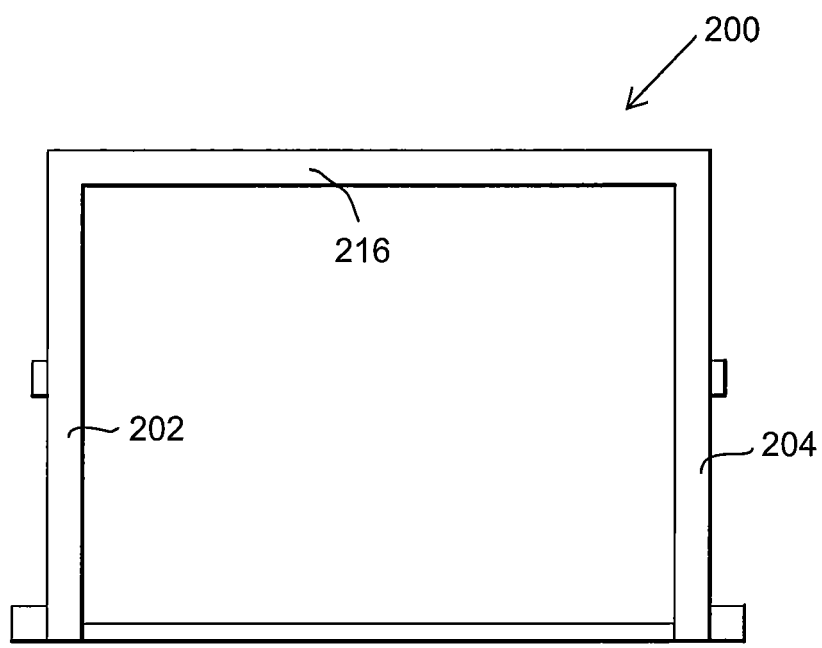
FIG. 22 is a front elevational view of an alternate embodiment of a ventilator power supply carrier constructed in accordance with the present invention.
Figure 23:
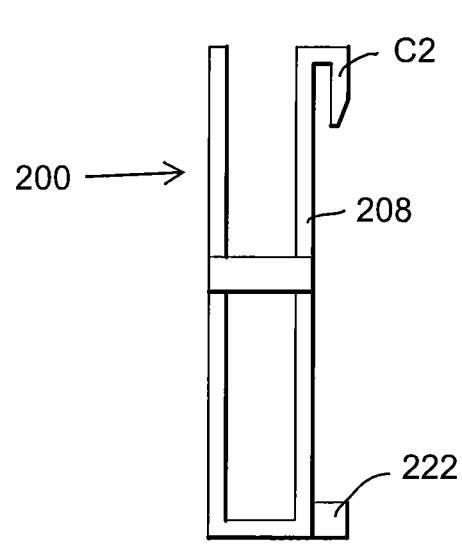
FIG. 23 is a right side elevational view of the ventilator power supply carrier shown in FIG. 22.
Figure 24:
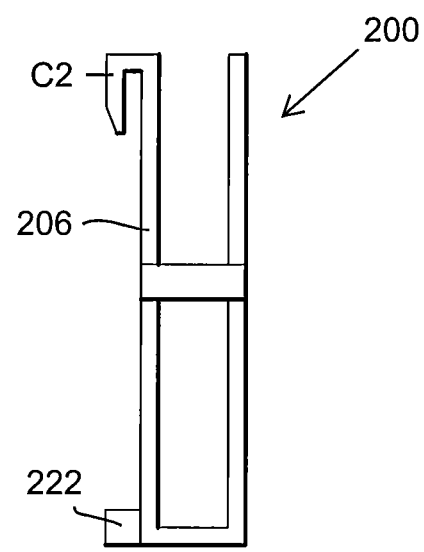
FIG. 24 is a left side elevational view of the ventilator power supply carrier shown in FIG. 22.
Figure 25:
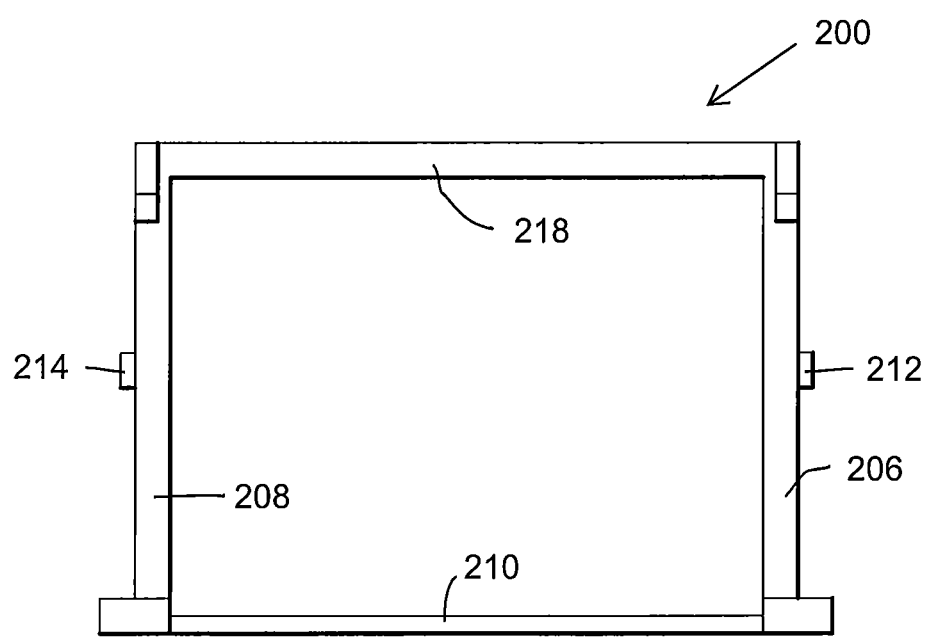
FIG. 25 is a rear elevational view of the ventilator power supply carrier shown in FIG. 22.
Figure 26:
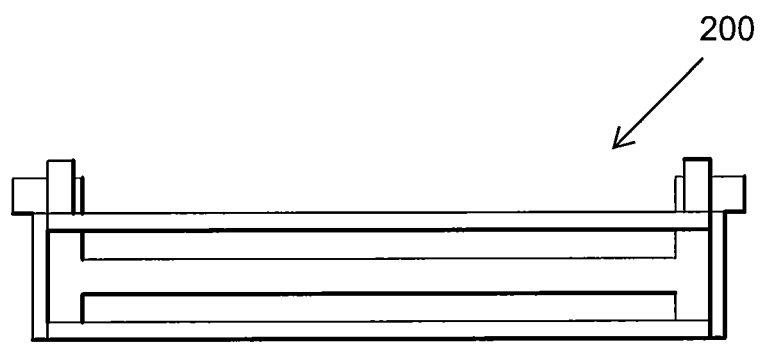
FIG. 26 is a top plan view of the ventilator power supply carrier shown in FIG. 22.
Figure 27:
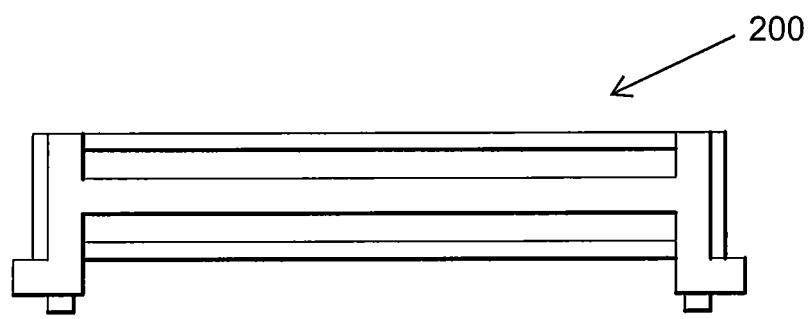
FIG. 27 is a bottom plan view of the ventilator power supply carrier shown in FIG. 22.
Figure 28:
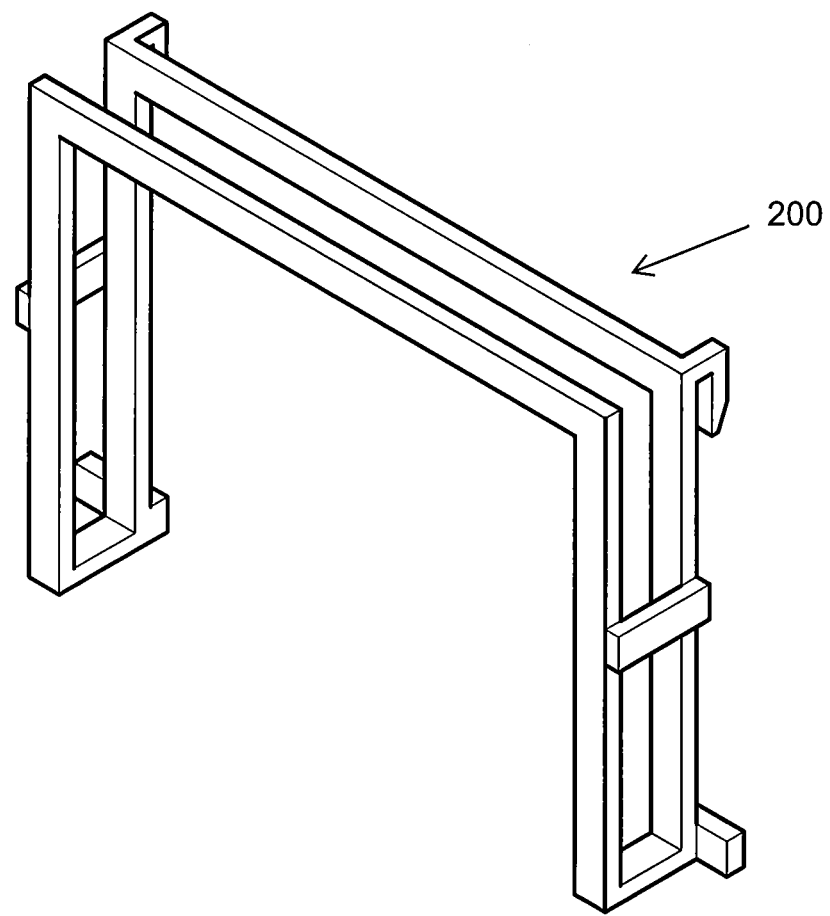
FIG. 28 is a rear perspective view of the ventilator power supply carrier shown in FIG. 22.

FIG. 11 illustrates carrier 48 detached from bracket 80, and power supply 50 removed from a compartment, or, receiver portion R1 of carrier 48. Receiver R1 is sized to receive a battery, or some other power supply, and in one preferred embodiment is at least 18 cubic inches in volume. FIGS. 12, 13, and 14 show, respectively, a top plan view, front elevational view and left side elevational view of carrier 48. Carrier 48 could be of similar construction as discussed above in regards to carrier 12.

FIGS. 15-21 and 29-41, illustrate an alternate embodiment respiratory ventilator, generally 100. Carrier 100 includes front and rear uprights 102 and 104, side members 106, 108, a bottom member 110, bottom side members 112, 114, front members 116 and 118, and rear member 120.

Carrier 100 also includes a receiver R3 formed by uprights 102 and 104, bottom 110, side members 106, 108, front members 116 and 118, and rear member 120 for receipt of a respirator ventilator V.

Figure 32A:
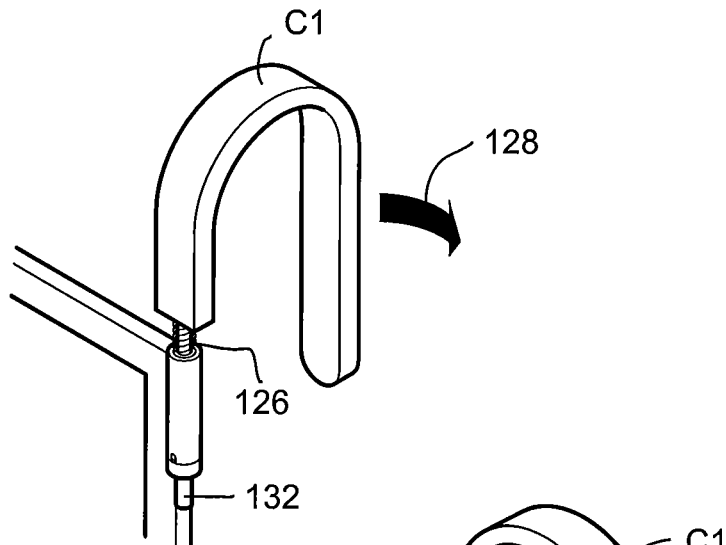
FIGS. 32A-32C are perspective views of a connector, or, coupling, of the ventilator carrier shown in FIG. 15, moving between different positions.
Figure 32B:
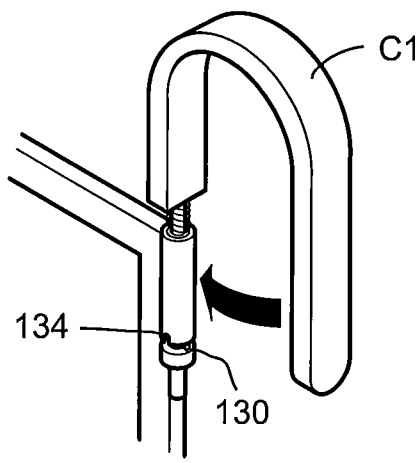
Figure 32C:
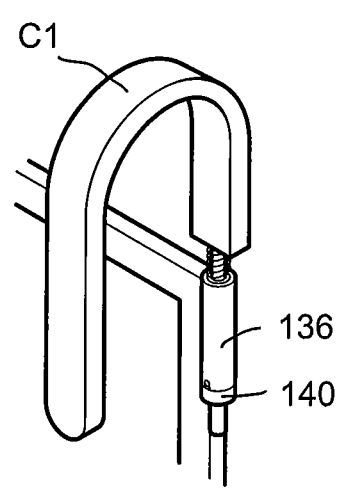
Figure 33:
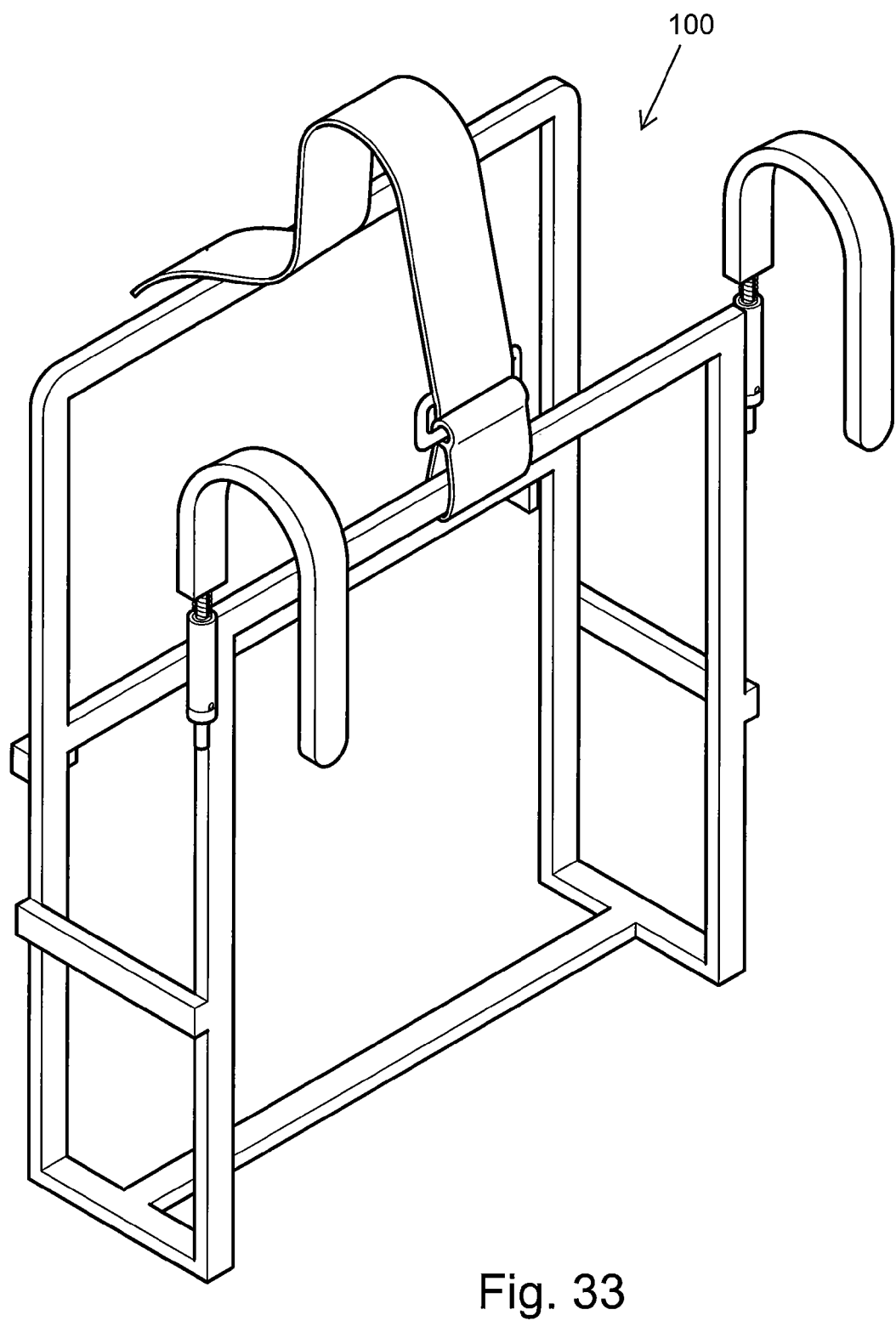
FIG. 33 is rear perspective view of the ventilator carrier shown in FIG. 15.

Connected at upper portions of rear uprights 104 are pivoting couplers, generally C1, which can be pivoted from the position shown in FIG. 32A to the positions in FIGS. 32B and 32C. Such pivoting is performed by depressing coupling C1 against the force of a spring 126, which in one preferred embodiment is a coil spring, and rotating coupling C1 in the desired direction, such as in the direction of arrow 128 in FIG. 32A. When coupling C1 moves through the intermediate position shown in FIG. 32B, and arrives at the position in FIG. 32C, coupling C1 can be released, and spring 126 would force coupling C1 upwardly such that a pin 130 on a plunger 132, which is encircled by coil spring 126 and which is connected to coupling C1, registers with a notch 134 of a sleeve 136 attached to rear upright 104. This registration of pin 130 in notch 134 locks coupling C into this position, where it remains until depressed and again rotated to the position shown in FIG. 32A or at some other desired position. A collar 140 is provided on plunger 132 and captures plunger 132 to prevent it from being pushed upwardly out of sleeve 136, due to the force of spring 126. The interaction of plunger 132 and sleeve 136 provides a pivotal connector for coupling C1.

The ability to rotate couplings C1 improves the versatility of carrier 100 in that there may be occasions where it would be more desirable to hang carrier 100 with coupling members C1 facing towards the front of carrier 100, rather than to the rear or carrier 100. Also, there may be occasions where it would be desirable to have one coupling C1 facing toward the front, and the other coupling C1 facing towards the rear of carrier 100, depending on the location where carrier 100 is to be installed.

It is to be understood that one or more couplings C1 could also be positioned at the intermediate position shown in FIG. 32B, or some other position, with pin 130 registering with a notch (not shown) in order to selectively lock such coupling C1 into place.

Figure 34:
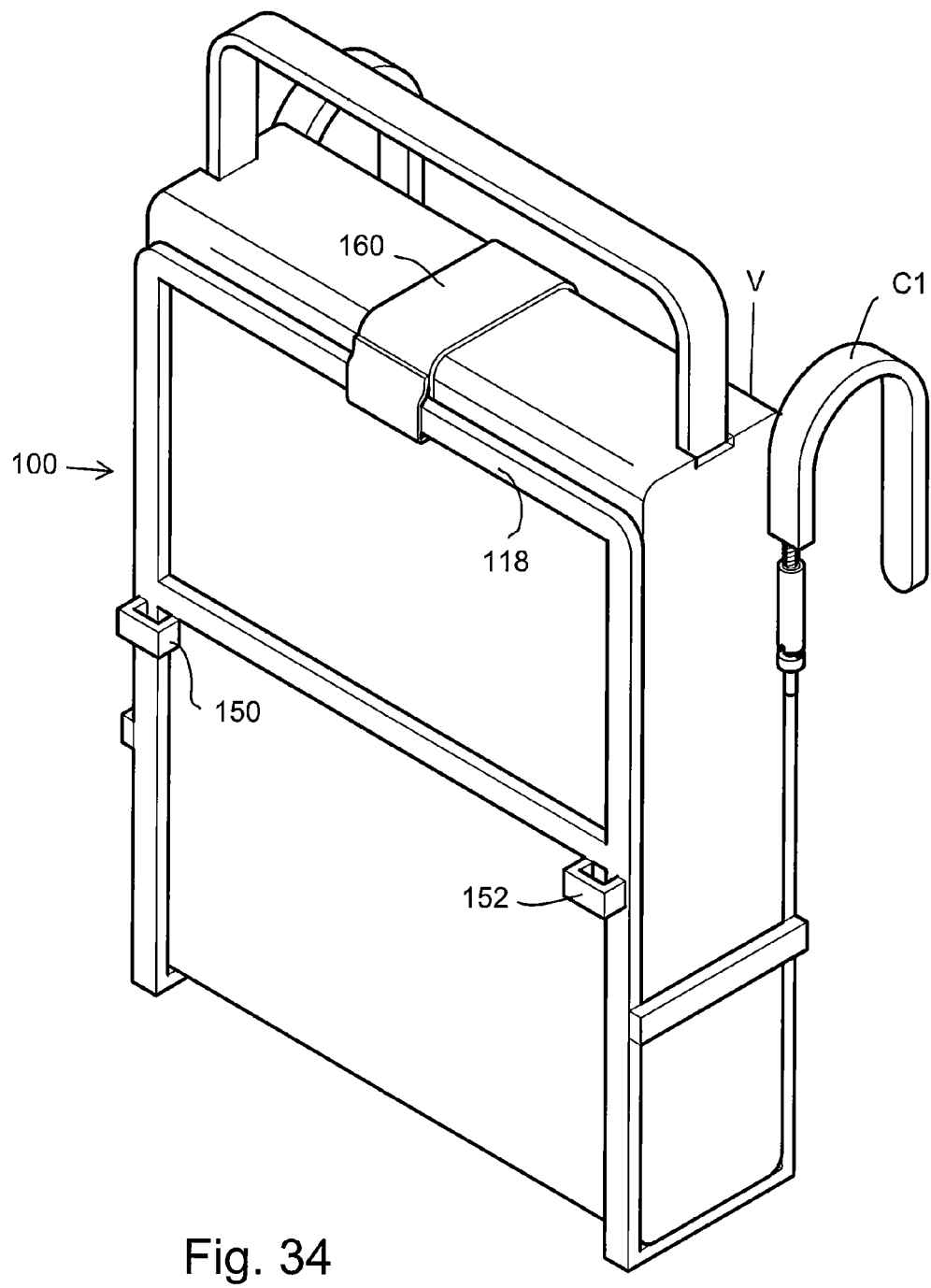
FIG. 34 is front perspective view of the ventilator carrier shown in FIG. 15, having a ventilator device therein.
Figure 35:
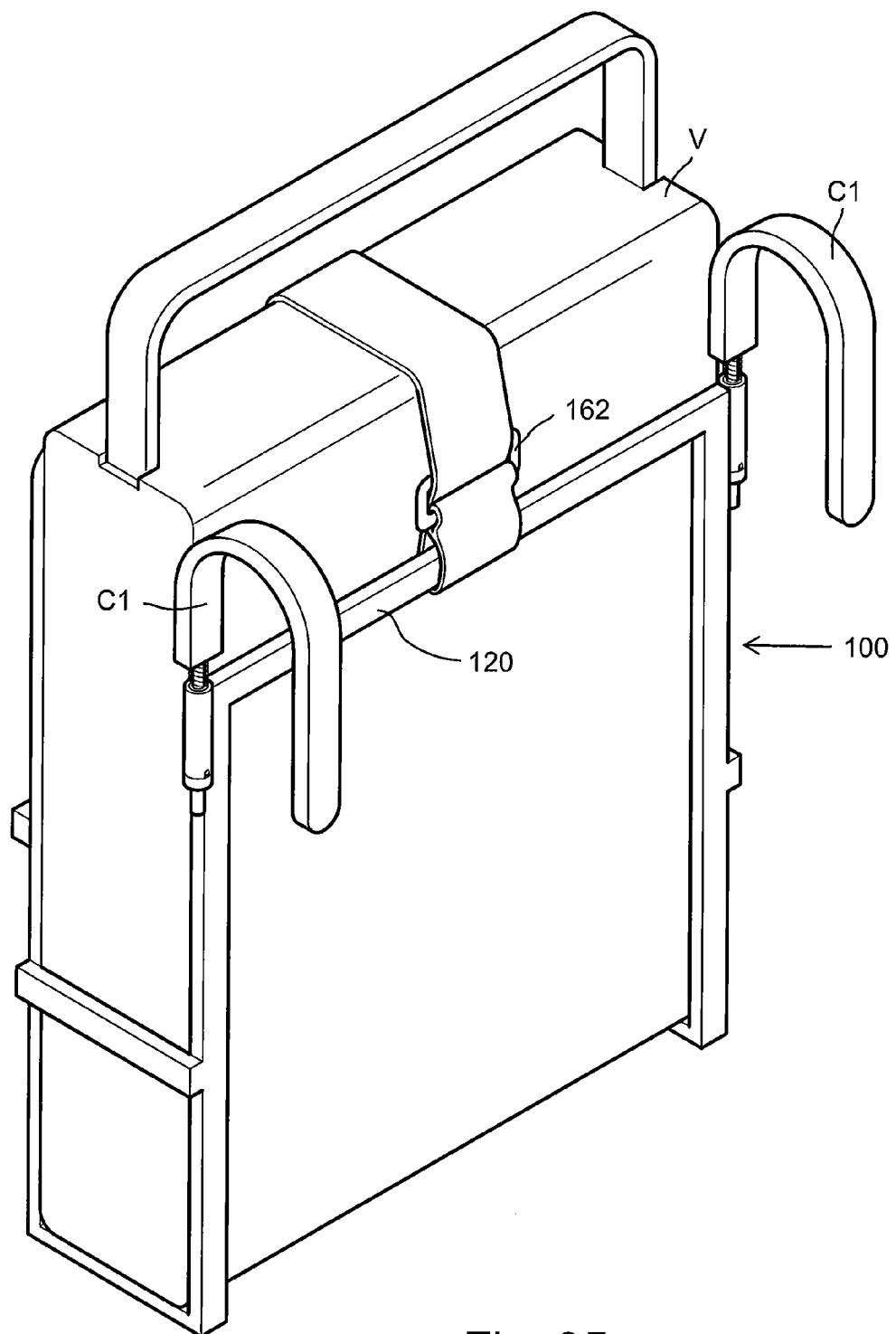
FIG. 35 is rear perspective view of the ventilator carrier shown in FIG. 15, having a ventilator device therein.

Carrier 100 also includes connected to front member 116 portions, or receptacles 150, 152, which extend outwardly from front member 116 (in a direction away from receiver portion R) for receipt of a power supply carrier, generally 200, discussed below. As shown in FIGS. 34 and 35, a ventilator V is received in receiver R3 of carrier 100 and is held there by a strap 160 having a buckle arrangement 162, the strap extending between rear member 120 and front member 118.

Figure 36:
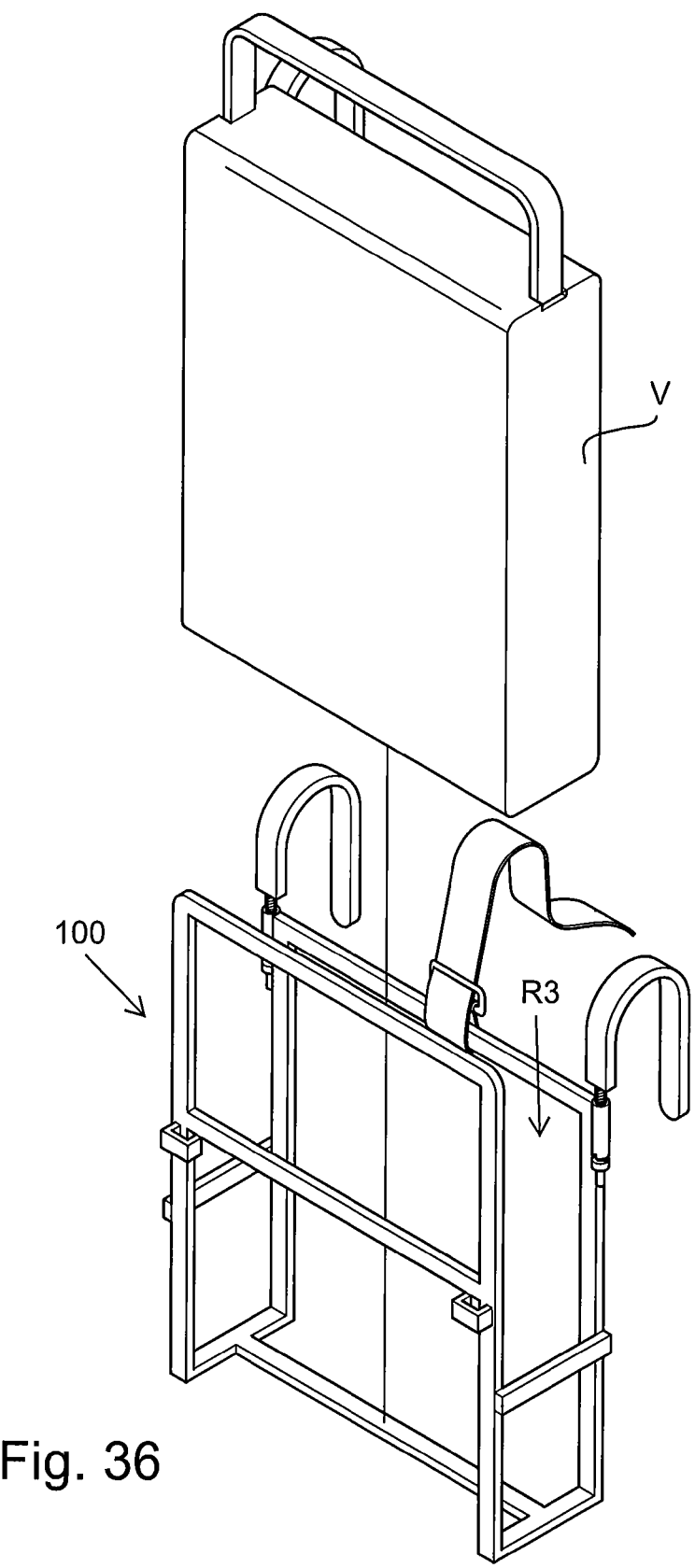
FIG. 36 is a perspective view of the ventilator carrier shown in FIG. 15, with a ventilator device in the process of being positioned therein.
Figure 37:
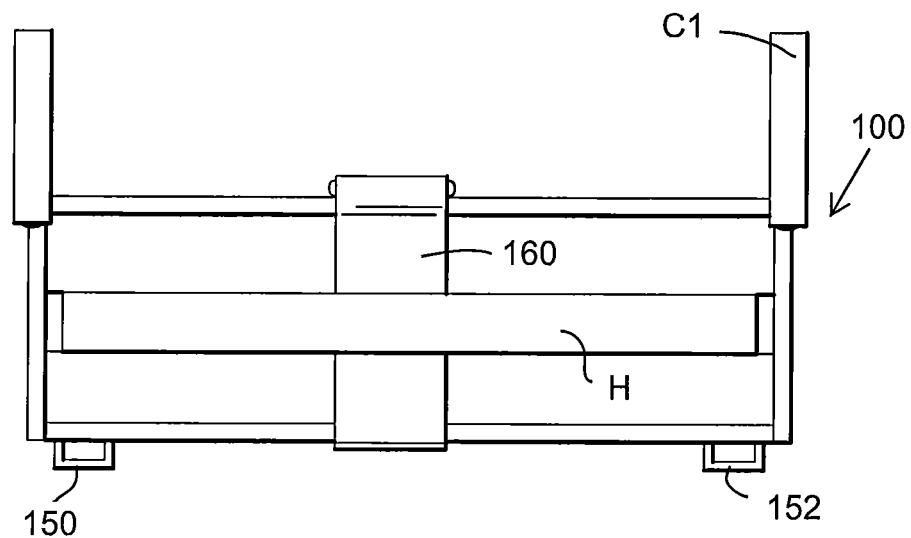
FIG. 37 is a top plan view of the ventilator carrier shown in FIG. 15, with a ventilator device positioned therein.
Figure 38:
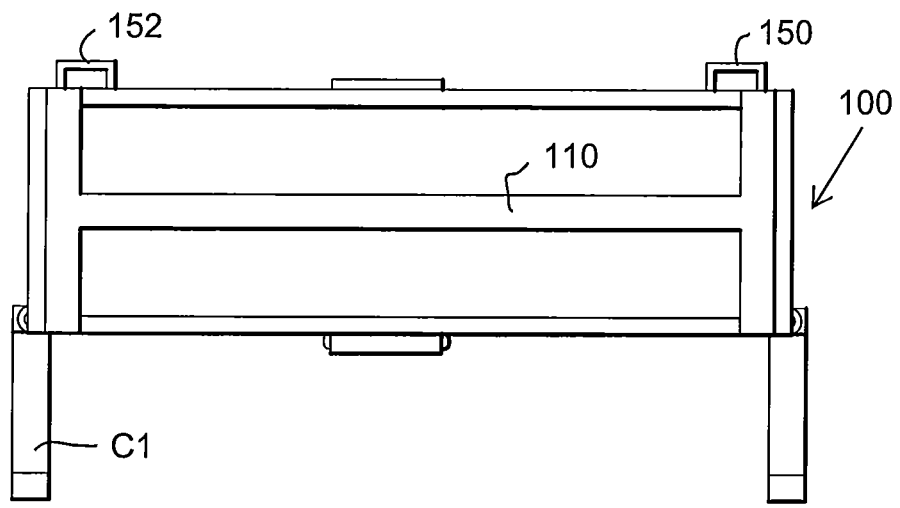
FIG. 38 is a bottom plan view of the ventilator carrier shown in FIG. 15, with a ventilator device positioned therein.
Figure 39:
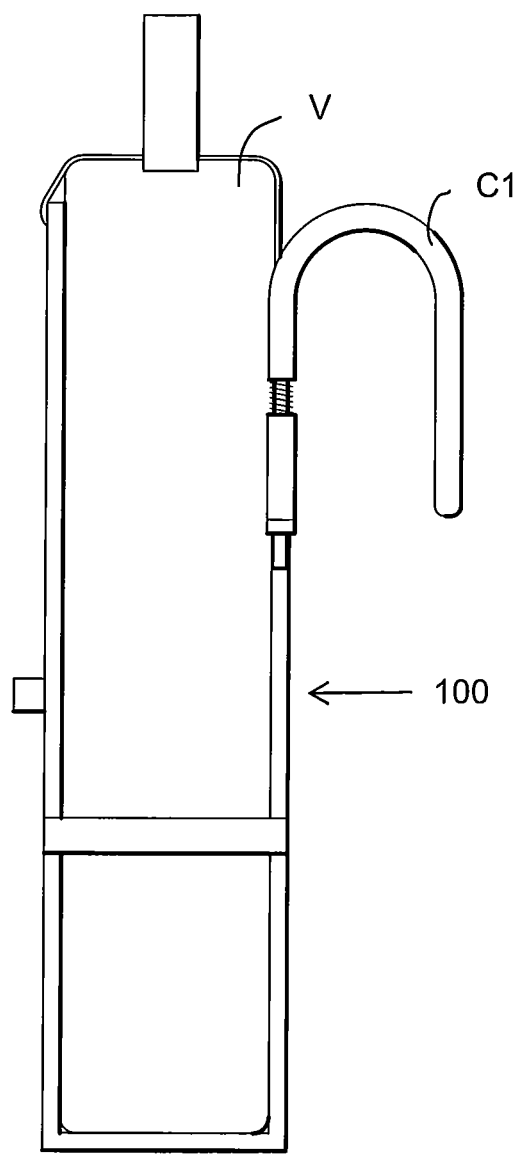
FIG. 39 is a right side elevational view of the ventilator carrier shown in FIG. 15, with a ventilator device positioned therein.
Figure 41:
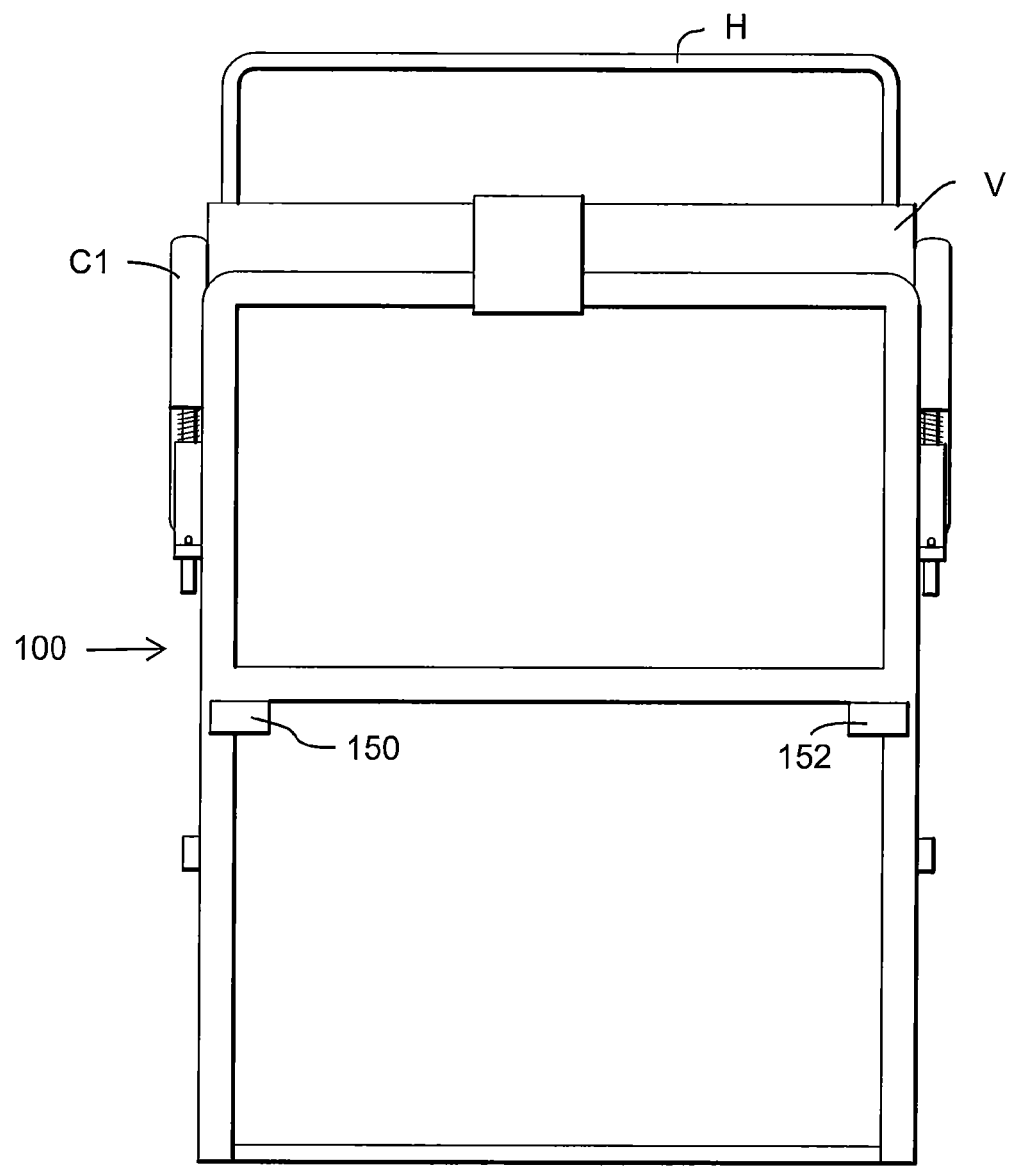
FIG. 41 is rear elevational view of the ventilator carrier shown in FIG. 15, with a ventilator device positioned therein.

FIG. 36 illustrates ventilator V being in a position removed from receiver R3, while FIGS. 39 and 41 illustrate ventilator V from right elevational and rear elevational, respectively, views.

FIGS. 22 through 28 illustrate an alternate embodiment power supply carrier, generally 200, constructed in accordance with the present invention. Carrier 200 includes front uprights 202 and 204, rear uprights 206, 208 (FIG. 25), a bottom member 210, side members 212, 214, a front member 216, a rear member 218, and hook-like connectors, or couplings, generally C2, connected or carried on the upper ends of rear uprights 206, 208.

Figure 29:
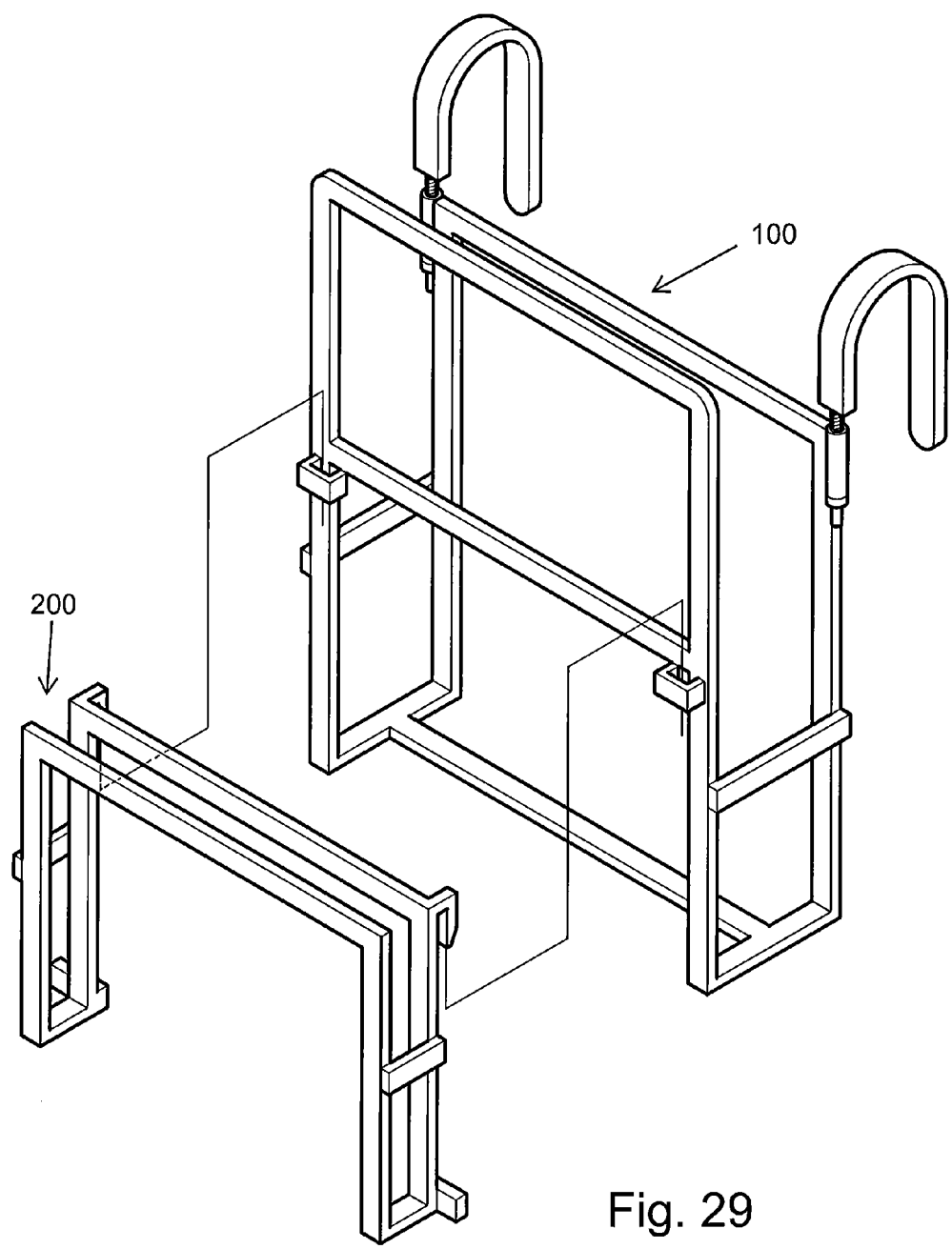
FIG. 29 is an exploded view of the ventilator carrier shown in FIG. 15 and the ventilator power supplier carrier shown in FIG. 22.
Figure 30:
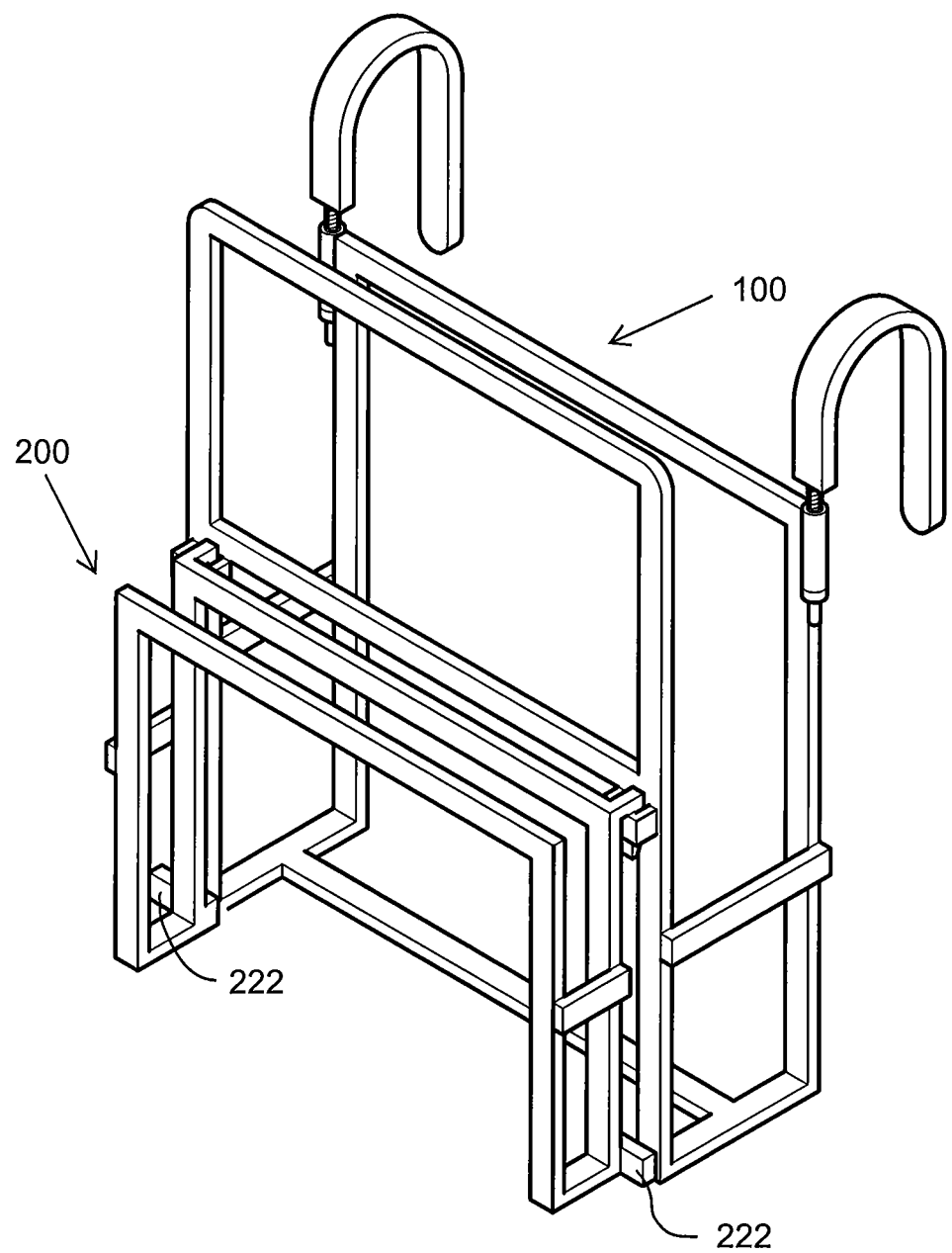
FIG. 30 is front perspective view of the ventilator power supplier carrier shown in FIG. 22 attached to the ventilator carrier shown in FIG. 15.
Figure 31:
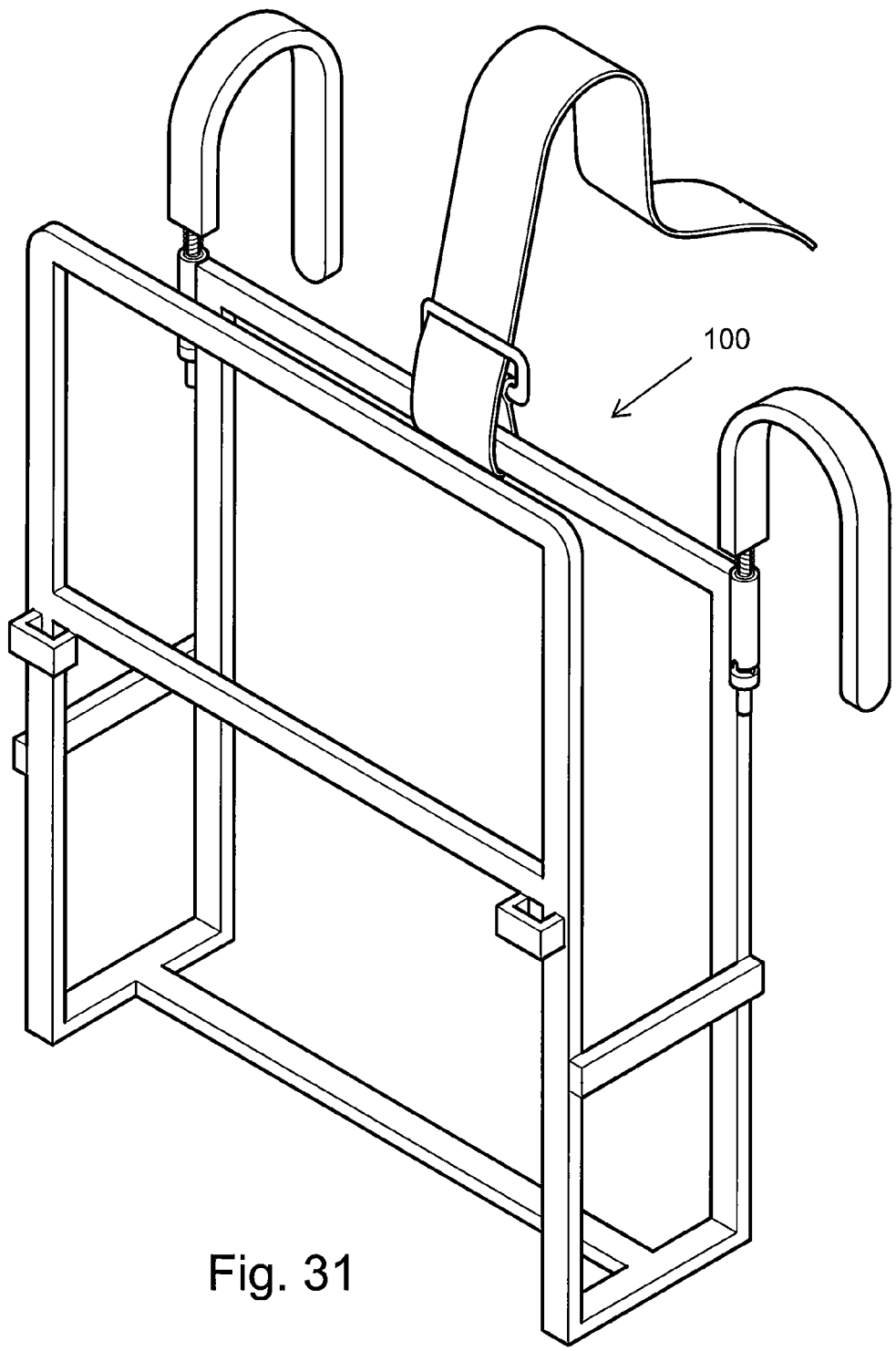
FIG. 31 is front perspective view of the ventilator carrier shown in FIG. 15.

FIG. 29 shows power supply carrier 200 detached from ventilator carrier 100, and FIG. 30 similar drawing showing, however, carrier 200 being readily demountably coupled with ventilator carrier 100 through engagement of couplings C3 of carrier 200 with receptacles 150, 152 of carrier 100. Spacers 222 provided on rear uprights 206, 208, maintain carrier 200 in a generally parallel relationship with ventilator carrier 100.

The couplings C, C1, and C2 of the present invention discussed above are preferably placed at a position spaced from the generally vertical centerline of the carrier to which such couplings are attached. The couplings are spaced away from such centerline in the same direction as it is desired to have the lower portion of such carrier swing in the event such lower portion is unrestrained from movement. For example, placement of the couplings on the backside of a carrier (whether a ventilator carrier, power supply carrier, or a carrier used for some other purpose) spaced from the centerline of such carrier, would cause the lower portion of such carrier to rotate rearwardly, with respect to the front of the carrier.

Accordingly, if the carrier is attached, for example, to the rear of a seat of an inclinable wheelchair, the lower portion of such carrier would tend to be moved towards the back of such seat as the seat reclines (and away from the back of such seat as the seat is returned from the reclined position). This allows the carrier to remain generally close to, and perhaps generally parallel with, the seatback of such wheelchair as the seatback reclines. This also reduces the likelihood of such carrier swinging out away from the seatback as it reclines, thereby maintaining the carrier in a low profile relationship with the seatback. The carrier, by being readily demountably attached to the seatback, can easily be placed on and removed from the seatback as desired.

If, on the other hand, such carrier was allowed to swing outwardly from the seatback when the seatback reclined, the carrier could be more prone to being hit, knocked loose, or to provide an obstruction as the wheelchair maneuvers about.

The open framework structure of the ventilator carriers of the present invention preferably allow continual visual contact with the displays, readouts, and controls, of the ventilator when in use. Similarly, the power supply carriers of the present invention preferably allow the power supply to be changed and/or charged without removing the ventilator, the ventilator hoses, etc.

Because of the hook-like open couplings C, C1, and C2 found in preferred embodiments of the carriers disclosed herein, such carriers can be readily placed and/or removed from a support member S in vehicle, aircraft, hospital beds, etc., without further fastening devices being required. However, such couplings are not to be limited to the couplings shown herein, and could take on different forms and/or configurations without departing from the teachings of the present invention. For example, the couplings could include spring-loaded plates or members such as found on safety hooks (not shown) to prevent such couplings from becoming inadvertently detached from a support member S.

The open framework of the carriers of the present invention also reduces the likelihood of undesirable heat buildup in ventilators and batteries.

It is to be understood that carriers as disclosed herein can be used for carrying devices other than the ventilators and batteries discussed above. Specifically, a power supply could be carried in a ventilator carrier as discussed above, if desired.

While preferred embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the spirit or scope of the following claims.

What is claimed is:

1. A device for attaching a respiratory ventilator and a respiratory ventilator power supply to a support of a movable conveyance, such support being reclinable from a first position to a second position, the device comprising:
    a carrier having a generally open framework, including:
        a front portion and a rear portion opposite said front portion;
        said front portion and said rear portion defining a receiver therebetween that receives the respiratory ventilator;
        said front portion including a first front rail and a second front rail;
        said rear portion including a first rear rail and a second rear rail;
        said first rear rail terminating in a generally semi-circular first coupling;
        said second rear rail terminating in a generally semi-circular second coupling;
        a first side rail extending between said first front rail and said first rear rail;
        a second side rail extending between said second front rail and said second rear rail;
        a first bottom rail extending between said first front rail and said first rear rail;
        a second bottom rail extending between said second front rail and said second rear rail;
        a third bottom rail extending between said first bottom rail and said second bottom rail;
        a first pivotal connector that permits said first coupling to pivot with respect to said first rail between a locked position and an unlocked position;
        a second pivotal connector that permits said second coupling to pivot with respect to said second rail between a locked position and an unlocked position;
        a first spring that biases said first coupling towards said locked position; and
        a second spring that biases said second coupling towards said locked position;
    a first power supply attachment portion and a second power supply attachment portion connected to said front portion of said carrier;
    said first power supply attachment portion and said second power supply attachment portion each extending outwardly from said front portion of said carrier in a direction away from said receiver;
    said carrier having an upper portion proximate said first coupling and said second coupling and a lower portion proximate said third bottom rail;
    said first coupling and said second coupling each being configured to engage the support of the movable conveyance and to cause said carrier to hang from and pivot readily about the support of the movable conveyance as the support moves between the first position and the second position;
    said first coupling and said second coupling each being configured to cause said lower portion of said carrier to move relative to and towards the support of the movable conveyance as the support reclines from the first position to the second position; and
    said first coupling and said second coupling each being configured to cause said lower portion of said carrier to move relative to and away from the support of the movable conveyance as the support moves from the second position to the first position.

2. The device of claim 1, wherein said first power supply attachment portion and said second power supply attachment portion are each configured to carry the power supply for the respiratory ventilator outwardly from said front portion of said carrier in a direction away from said receiver.

3. A device for attaching a respiratory ventilator and a respiratory ventilator power supply to the seatback of a wheelchair, such seatback being reclinable from a first position to a second position, the device comprising:
    a carrier having a generally open framework, including:
        a front portion and a rear portion opposite said front portion;
        said front portion and said rear portion defining a receiver therebetween that receives the respiratory ventilator;
        said front portion including a first front rail and a second front rail;
        said rear portion including a first rear rail and a second rear rail;
        said first rear rail terminating in a generally semi-circular first coupling;
        said second rear rail terminating in a generally semi-circular second coupling;
        a first side rail extending between said first front rail and said first rear rail;
        a second side rail extending between said second front rail and said second rear rail;
        a first bottom rail extending between said first front rail and said first rear rail;
        a second bottom rail extending between said second front rail and said second rear rail; and
        a third bottom rail extending between said first bottom rail and said second bottom rail;
    a first pivotal connector that permits said first coupling to pivot with respect to said first rail between a locked position and an unlocked position;

a second pivotal connector that permits said second coupling to pivot with respect to said second rail between a locked position and an unlocked position;

a first spring that biases said first coupling towards said locked position; and a second spring that biases said second coupling towards said locked position;

a first power supply attachment portion and a second power supply attachment portion connected to said front portion of said carrier;

said first power supply attachment portion and said second power supply attachment portion each extending outwardly from said front portion of said carrier in a direction away from said receiver;

said first power supply attachment portion and said second power supply attachment portion each being configured to carry the power supply for the respiratory ventilator outwardly from said front portion of said carrier in a direction away from said receiver;

said carrier having an upper portion proximate said first coupling and said second coupling and a lower portion proximate said third bottom rail;

said first coupling and said second coupling each being configured to engage said seatback and to cause said carrier to hang from and pivot readily about the seatback of the wheelchair as the seatback moves between the first position and the second position;

said first coupling and said second coupling each being configured to cause said lower portion of said carrier to move relative to and towards the seatback as the seatback reclines from the first position to the second position; and said first coupling and said second coupling each being configured to cause said lower portion of said carrier to move relative to and away from the seatback as the seatback moves from the second position to the first position.

4. A system for carrying a respiratory ventilator and power supply on at least one support of a wheeled conveyance, the support being inclinable, the device comprising:

a ventilator carrier defining a ventilator receiver that receives the respiratory ventilator;

a power supply carrier defining a power supply receiver that receives the power supply;

a power supply carrier coupling connected to said power supply carrier that readily demountably attaches said power supply carrier to said ventilator carrier;

a ventilator carrier coupling that readily demountably attaches said ventilator carrier to the support;

a hook-shaped portion connected to said ventilator carrier coupling that engages the support;

a pivotal connector that permits said hook-shaped portion to pivot with respect to said ventilator carrier between a locked position and an unlocked position;

a spring that biases said hook-shaped portion towards said locked position; and said ventilator carrier coupling being configured to cause said ventilator carrier to incline in response to, and generally to substantially the same extent as, the inclination of the support.

5. The system as defined in claim 4, further comprising:
said ventilator carrier being of a generally open framework configuration; and
said power supply carrier being of a generally open framework configuration.

6. The system as defined in claim 4, wherein said ventilator carrier comprises:
at least four upright rails;
at least one bottom rail;
at least two side rails;
a front rail;
a rear rail; and
said upright rails, said bottom rail, said two side rails, said front rail, and said rear rail being configured to form an open frame configuration defining said ventilator receiver.

7. The system as defined in claim 4, further comprising:
said ventilator carrier defining a front, a back, and a bottom and a centerline extending between said front and said back and generally perpendicular to said bottom;
said back defining an upper portion and a lower portion; and
said ventilator carrier coupling being spaced away from said centerline and attached to said upper portion of said back.

8. A device for carrying a respiratory ventilator and respiratory ventilator power supply on a support, the support being inclinable, the device comprising:
at least one body portion; said body portion defining:
   (i) a first receiver that receives the respiratory ventilator; and
   (ii) a second receiver that receives the respiratory ventilator power supply;
   (iii) a front;
   (iv) a bottom; and
   (v) a back defining an upper portion and a lower portion and a centerline extending along said back and generally perpendicular to said bottom;
at least one coupling connected to said body portion spaced away from and extending generally parallel to said centerline and upwardly beyond said back that attaches said body portion to the support;
a hook-shaped portion connected to said coupling that engages the support;
a pivotal connector that permits said hook-shaped portion to pivot with respect to said body portion between a locked position and an unlocked position;
a spring that biases said hook-shaped portion towards said locked position; and
said coupling being configured to cause said body portion to incline in response to, and generally to substantially the same extent as, the inclination of the support.

* * * * *